United States Patent [19]

French et al.

[11] Patent Number: 5,469,740

[45] Date of Patent: Nov. 28, 1995

[54] INTERACTIVE VIDEO TESTING AND TRAINING SYSTEM

[75] Inventors: Barry J. French, Bay Village; Kevin R. Ferguson, Broadview Heights; Halley A. McDonald, III, Cleveland, all of Ohio; Andrew B. Glass, Dix Hills, N.Y.; Timothy Mohansingh; Gregory Borges, both of Cleveland Heights, Ohio

[73] Assignee: Impulse Technology, Inc., Bay Village, Ohio

[21] Appl. No.: 984,337

[22] Filed: Dec. 2, 1992

Related U.S. Application Data

[63] Continuation-in-part of Ser. No. 380,157, Jul. 14, 1989, Pat. No. 5,099,702, and a continuation-in-part of Ser. No. 801,877, Dec. 3, 1991.

[51] Int. Cl.$^6$ ..................................................... A61B 5/22
[52] U.S. Cl. ...................... 73/379.04; 273/445; 482/901; 482/902
[58] Field of Search ........................... 73/379.04, 379.05, 73/865.4, 172; 273/445, 446, 148 B, 434, 438; 901/47; 244/161; 482/9, 14, 901, 902, 1, 8, 54; 364/413.01; 434/247, 258; 128/774, 779

[56] References Cited

U.S. PATENT DOCUMENTS

| | | | |
|---|---|---|---|
| 3,024,020 | 3/1962 | Alton | 434/258 |
| 4,463,946 | 8/1984 | Wallace et al. | 434/258 X |
| 4,720,789 | 1/1988 | Hector et al. | 273/DIG. 28 X |
| 4,917,373 | 4/1990 | Bourne et al. | 472/61 |
| 5,139,261 | 8/1992 | Openiano | 273/148 B |
| 5,209,240 | 5/1993 | Jain et al. | 434/258 X |

FOREIGN PATENT DOCUMENTS 9116954  11/1991  WIPO ......................................... 482/9

Primary Examiner—Richard E. Chilcot, Jr.
Assistant Examiner—Elizabeth L. Dougherty
Attorney, Agent, or Firm—Peter D. Sachtjen

[57] ABSTRACT

A testing and training system for measuring and assessing leg reaction movement sequence of a subject includes a test field having a plurality of load sensing target positions defining vectored movement paths for the subject, the field and target positions being replicated on a video screen positioned frontally with respect to the subject with visual cues presented on the screen directing movement between positions with hardware and software processing the cues and signals from the target positions to determine time intervals associated with changes in loading during the movement and determining reaction movement sequence parameters based thereon.

26 Claims, 31 Drawing Sheets

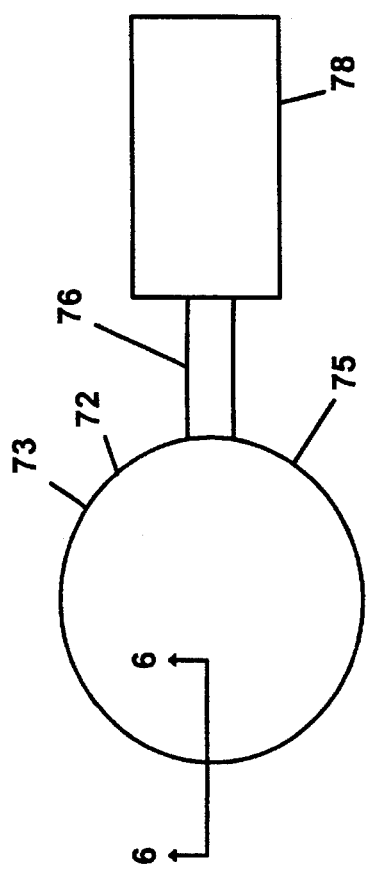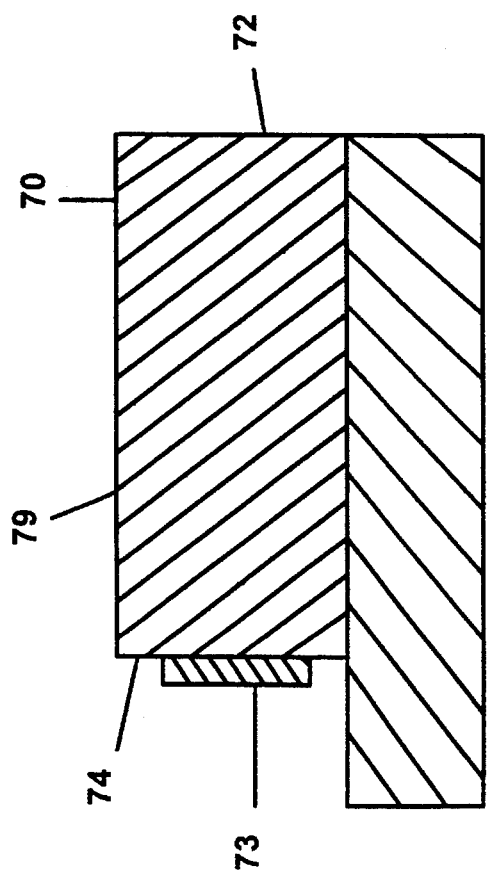

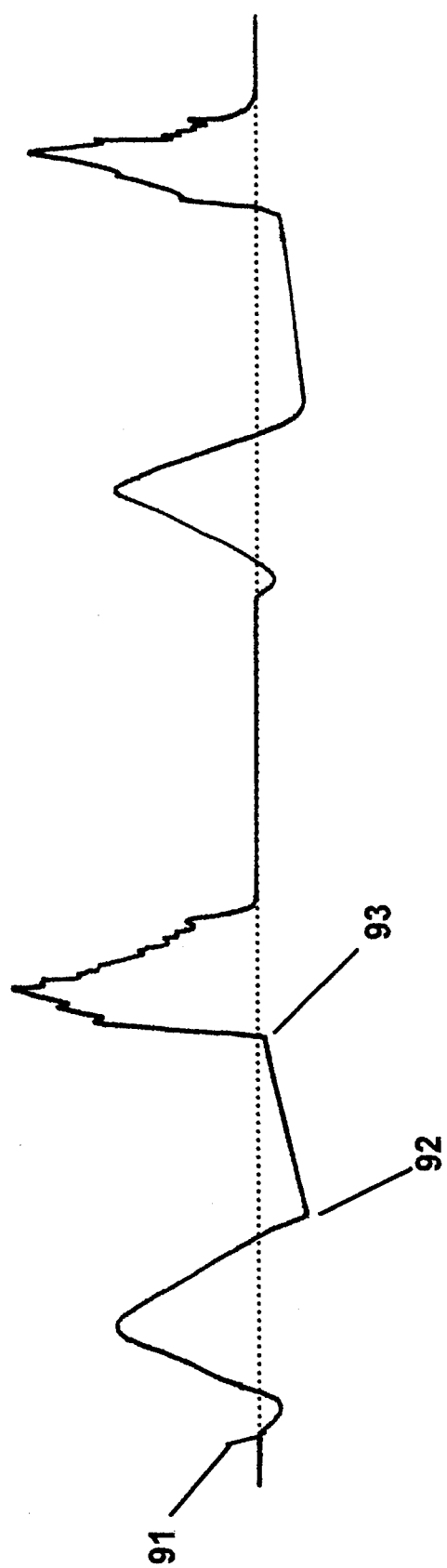

MOVEMENT SKILLS ANALYSIS

| MOVEMENT DIRECTION | REACTION TIME CONTACT TIME TRANSIT SPEED STABILITY TIME | MOVEMENT DIRECTION | REACTION TIME CONTACT TIME TRANSIT SPEED STABILITY TIME | DEFICIT % AND DIRECTION |
|---|---|---|---|---|
| FORWARD LEFT | 1.000 sec<br>0.500 sec<br>12.500ft/sec<br>2.500 sec | FORWARD RIGHT | 1.250 sec<br>0.625 sec<br>10.000ft/sec<br>3.000 sec | 25.0% FR<br>25.0% FR<br>26.0% FR<br>25.0% FL |
| BACKWARD LEFT | 2.000 sec<br>1.000 sec<br>8.000ft/sec<br>4.000 sec | BACKWARD RIGHT | 2.500 sec<br>1.250 sec<br>6.000ft/sec<br>3.000 sec | 25.0% BR<br>25.0% BR<br>26.0% BR<br>25.0% BL |
| LEFT LATERAL | 0.750 sec<br>0.375 sec<br>15.000ft/sec<br>1.600 sec | RIGHT LATERAL | 1.000 sec<br>0.500 sec<br>10.000ft/sec<br>2.000 sec | 33.3% R<br>33.3% R<br>33.3% R<br>33.3% L |
| COMPOSITE FORWARD | 1.125 sec<br>0.563 sec<br>11.250ft/sec<br>2.250 sec | COMPOSITE BACKWARD | 2.250 sec<br>1.125 sec<br>7.500ft/sec<br>3.500 sec | 100.0% B<br>99.8% B<br>37.8% B<br>55.5% B |
| AVG RT 1.525 | AVG CT 0.763 | AVG TS 9.800 | AVG ST 2.650 | |

FIG. 11

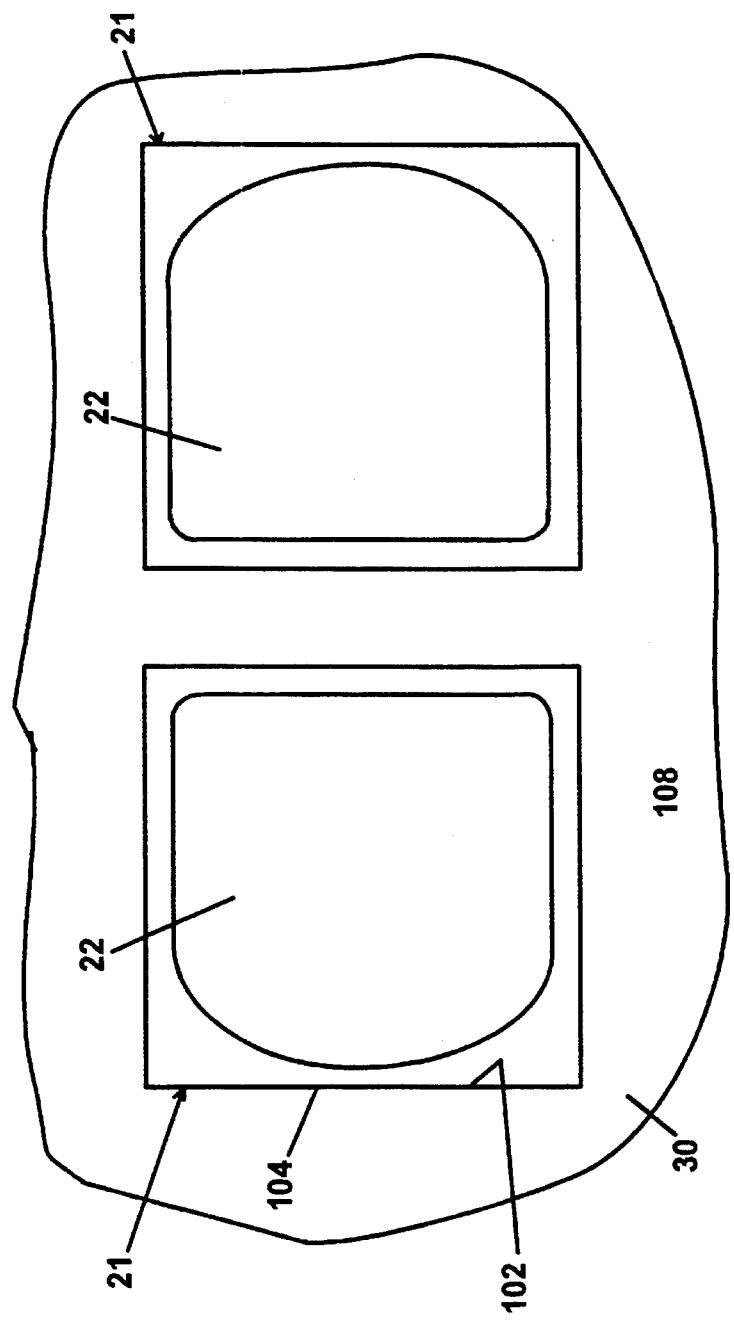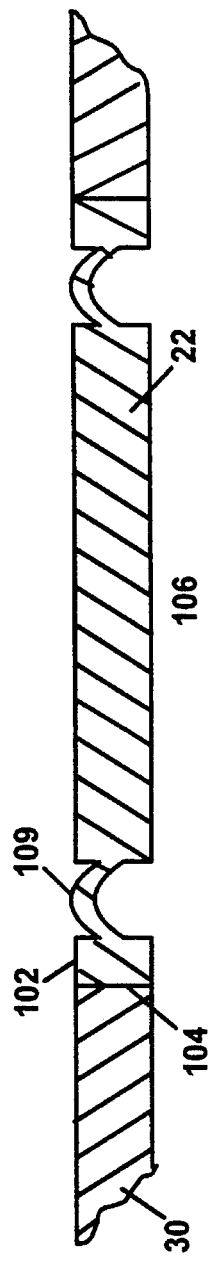

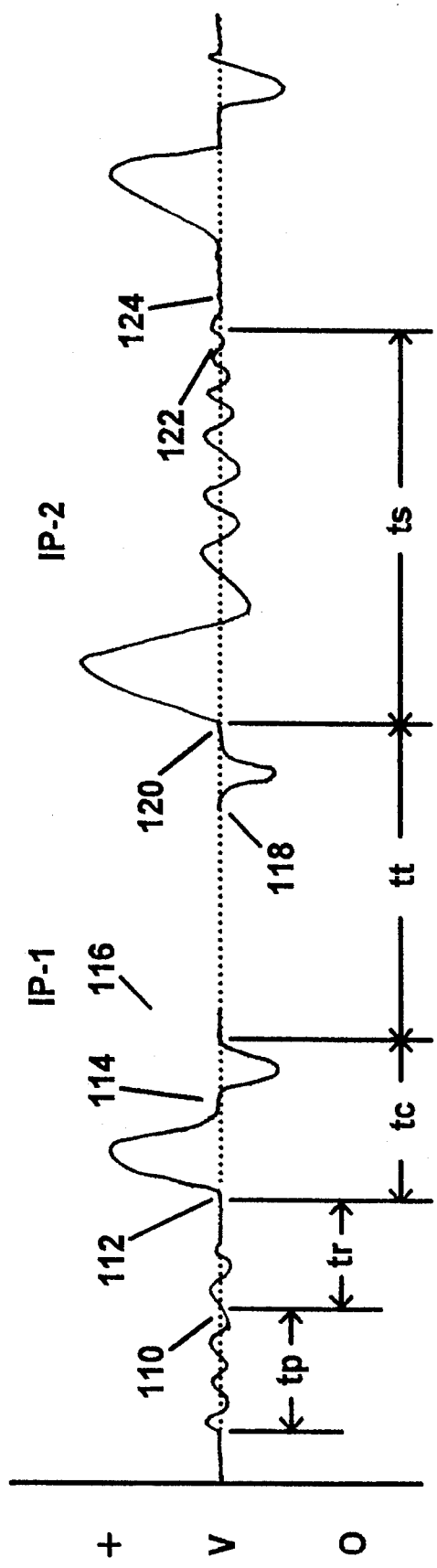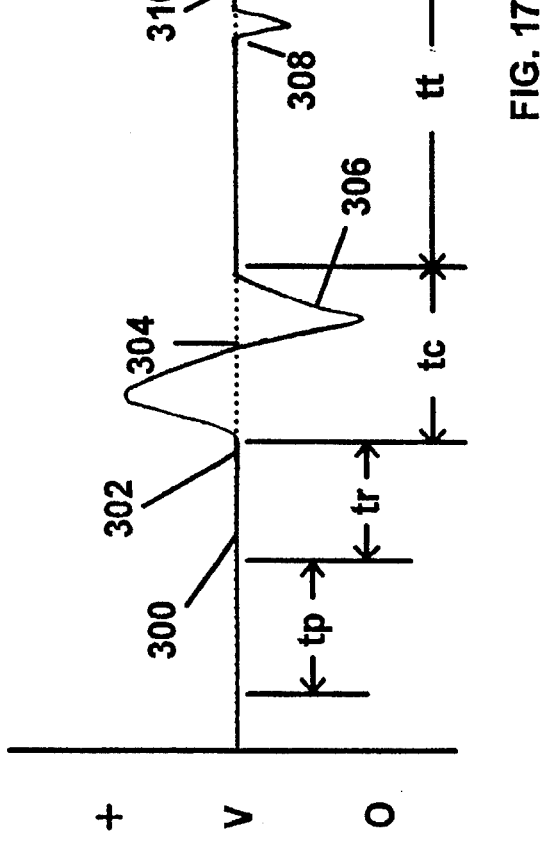
FIG. 14
FIG. 17

INTERACTIVE VIDEO TESTING AND TRAINING SYSTEM

CROSS REFERENCE TO RELATED APPLICATIONS

This application is a continuation in part of U.S. patent application Ser. No. 380,157 filed on Jul. 14, 1989, issued as U.S. Pat. No. 5,099,702 on Mar. 31, 1992, and U.S. patent application Ser. No. 801,877 filed on Dec. 3, 1991.

TECHNICAL FIELD

The present invention relates to testing and training systems for measuring and assessing participant movement and performance and, in particular, to an apparatus and method for directing and assessing the weight-bearing leg reaction movement sequence of participants. Moreover, the present invention provides testing and rehabilitation of weight-bearing capabilities through direct measurement and training of functional movement by measuring the magnitude and timing of forces applied to the ground during stance and movement.

BACKGROUND OF THE INVENTION

Inherent in most sports, and in many demanding workplace situations, is a distinct weight-bearing leg reaction movement sequence that must be quickly and accurately executed in response to the actions of an opponent, movement of a ball, or other visual cues and stimuli that cannot be predicted by the subject. When optimally executed, the reaction movement sequence will allow the individual to shift the body's center of gravity from its current position to a visually identified target or intercept position in the shortest possible time. As a result of injury, disease processes, musculoskeletal asymmetry or inappropriate training—the ability to initiate and coordinate weight-bearing movement may be compromised. Any dysfunction that affects muscular strength, power, endurance, coordination/agility, neurophysiologic function, musculoskeletal integrity or joint stability will affect movement to some degree.

In contrast to simple straight ahead running, a reaction movement sequence covers short distances—typically three to ten feet—and combinations of lateral, forward and backward movements. Athletic competitions are comprised of a multiplicity of movement sequences in response to the actions of an opponent, movement of a ball, or other visual cues and stimuli that cannot be predicted by the player. Few capabilities are more generic to athletics than quickness of movement to avoid or intercept an opponent or ball, generally short distance combinations of lateral, backward and forward motion, direction changes, and reaction movements. Undertaking the sequence requires perception and interpretation of a cue, decisions on optimal foot movement pattern and direction, and neuromuscular actuation response time and force output control to accelerate and decelerate body mass in any direction from the starting position. The reaction movement sequence may also require a quick change of direction towards a new intercept position, or stabilizing the body's center of gravity at the intercept position in order to best perform an action such as catching or throwing a baseball or executing a tennis backhand. Numerous examples of this react/shift/stabilize or react/shift/change direction movement sequence exist in almost all athletic activities involving a ball or team play and in many potentially injurious workplace situations.

Experts readily acknowledge that an athlete's capabilities to react, or any worker in physically demanding situations, and to accelerate and decelerate in any movement direction while maintaining appropriate balance and stability are among the most significant determinants of performance. Yet as critical as this reaction movement sequence is to successful play, and for on-the-job safety, heretofore there has not been available a system for measuring the individual components of a reaction movement sequence.

The quantifiable components of the reaction movement sequence may be defined as follows:

1. Reaction Time—The elapsed time from the appearance of a visual cue to a change in loading (force output to the ground) initiating the takeoff movement. This includes the time required to perceive the cue, interpret the required functional response in terms of direction and distance, and the neuromuscular activation time to initiate appropriate muscular contractions. Reaction time is not dependent on strength—the change in applied force that triggers reaction time measurement is very small. Unplanned movements may use different motor pathways and create different musculoskeletal stresses than pre-planned movements. Deficits in Reaction Time most likely result from one or a combination of the following factors: perception/interpretation problems that delay the movement decision; motor pathway dysfunction that affects neuromuscular activation time to initiate appropriate muscular contractions; pain, instability or other deterring sensation when a forceful movement is made in the deficit direction; lack of confidence in the capability of the injured limb that results in conscious or unconscious hesitation to move in the specified reaction direction.

2. Contraction Time or Ground Force Time—The elapsed time from initial change in loading until sufficient muscular force is generated to lift off initial weight-bearing position. This provides a means for reliably measuring the key component of functional muscular contraction time and for testing joint function during maximum effort takeoffs in different movement directions. Deficits in Ground Force Time most likely result from one or a combination of the following factors: instability, pain or other deterring sensations that prevent the subject from applying forces required to move quickly in the indicated direction; insufficient rehabilitation of equal strength and power in the involved extremity. The actual force during acceleration can also be quantified from the analog waveform.

3. Transit Time—The time from the instant of change in loading initiating the takeoff movement to full contact at the intercept position. Transit Speed is the distance traveled divided by time from the instant of force output initiating the takeoff movement to the instant of full contact at the target or intercept position. Transit time and thus transit speed is highly dependent on both muscular power acceleration and optimization of foot movement pattern for the direction and distance to be covered. Transit speed is dependent on muscular power, but is even more affected by basic agility and optimization of foot movement pattern for the direction and distance to be covered. Improving transit speed is usually more a matter of practice and appropriate coaching than of specific rehabilitation programming.

4. Stabilization Time—The elapsed time from the instant of full contact at the target position to the moment that a stable stance is achieved, i.e., the time required for the individual to assume a stable stance after arriving at the target or intercept position. From the standpoint of sports performance, this measurement is designed to evaluate an athlete's ability to stabilize following rapid movement to an intercept position in order to best perform a task such as a catch and throw, tennis backhand or blocking maneuver. It is important to note that Stabilization Time is a new measurement construct that has had insufficient study to optimize threshold and window settings. However, it is expected to provide immediate value by allowing comparisons to be made using controlled, repeatable measurement criteria. Deficits in Stabilization Time likely result from one or a combination of the following factors: pain or instability in that compromises the subject's ability to decelerate body mass with the deficit limb insufficient rehabilitation of the plyometric/eccentric components of muscular performance; proprioception problems that result in prolonged stance or center of gravity corrections requiring muscular contractions that are measured as ground force changes; true balance problems that result in sway. Even small, low frequency forefoot to rearfoot or right to left weight shifting may result in ground force variations that are measured as longer ST's. The Stabilization Time measurement is not affected by bilateral weight distribution—its criteria are changes in ground force and time. This measurement uses threshold and window settings which can be adjusted by the clinician. The threshold setting is for magnitude of ground force variation (magnitude of oscillation or instability). The other setting is for duration of sample. The system measures how large the variations in force are over a specific time period or window. Measurement continues until no measured force variation greater than the threshold magnitude occurs in a single time window. Essentially, the system looks at stability over very small periods of time until the specified level of stability is maintained for an entire specified period. Stability Time measurement can be made less demanding (faster subsequent movement cues) by increasing the force variation threshold and shortening the time window.

5. Stabilization Index—The number of times ground force oscillations exceed a selected magnitude in a specified time period. Both the magnitude and duration "windows" are adjustable using the same utility as for Stabilization Time above. On landing from a vertical drop, or medial, lateral, forward or backward movement, the limb is required to absorb the impulse loads required to decelerate body mass which quickly decrease to stable weight-bearing load. During this period of loading change, the large initial spike in ground force is followed by a series of force variations (oscillations) which have a magnitude and frequency pattern that is affected by musculoskeletal factors. It is expected that a limb with "good" stability—i.e., intact and strong primary static restraints—will show a quite different magnitude and frequency pattern than a limb that is relying more on secondary, dynamic restraints to control joint integrity. If clinical trials bear out these expectations, an optimized stability index will provide a means for testing of functional stability and the documentation of surgical, rehabilitation and bracing treatments.

6. Ground Time—The time from instant of ground contact to the instant of takeoff. This is a key measure of plyometric/eccentric capability and is completely differentiated from Ground Force Time which is taken from a stable position on the platform. Plyometric performance capability is a reliable indicator of how efficiently the body uses the stored elastic energy of muscle and is also an indicator of neuromuscular efficiency in controlling muscle contraction. Ground Time allows quantification and comparison of one of the most important aspects of plyometric performance. Deficits in Ground Time will almost certainly result from any pain or instability, but otherwise are the result of insufficient plyometric/eccentric training.

7. Total Movement Time—The total time required to complete a specific programmed set or sequence of movements. This measurement appears in tests like the Single Leg Reaction/Stabilization Hop Test. This test can be performed with forward, medial, lateral or even backward hops. In the test for which Total Movement Time is reported, a number of other breakout measures such as best and average Ground Force Time may also be reported. Deficits in Total Movement Time may result from deficits in one or more of these individual factors. TMT is reported to give a composite or sum deficit which is expected to be a useful indicator of overall functional limitation in activities incorporating movements similar to the demands of the testing protocol. Individual deficits should be helpful in designing the rehabilitation protocol using concepts similar to those discussed above.

8. Jump Height—Height of vertical jump to within ½ inch. Maximum vertical jump is an excellent indicator of peak muscular power output and correlates well to overall athletic performance capability for many sports. Vertical jump height can be tested in many ways, but only a force platform can measure how quickly an athlete reacts and gets off the ground. The force/time transducer platform quantifies the following factors; Jump Height; Reaction Time; Takeoff Time, the time from instant of vertical jump cue to instant of takeoff; Total Jump Time from jump cue to takeoff (overall, a quicker takeoff is often more important than jump height). The duration of the eccentric and concentric phases of jump or horizontal acceleration can also be quantified.

When measuring transit rates over short distances, two critical components comprise the elapsed time from visual cue to arrival at the intercept position; the reaction time, and the transit time. The reaction time can be a significant portion of the total elapsed time. For example, the reaction time will typically vary between 0.2 to 0.4 seconds, and the transit time, predicated on the distance and direction traveled can vary from 0.5 to more than a second. Therefore, without the ability to accurately and reproducibly measure reaction time and separate it from the total elapsed time, the coach, trainer or clinician would be unable to determine the real transit time, and thus, discern the source of any deficiency.

Additionally, reaction time can be an important parameter to consider when evaluating an athlete's recovery from any injury. For example, though an athlete may have recovered physically from an injury, he may not have yet regained the confidence to explode off the injured limb. Any hesitation would be reflected in increased or longer reaction times.

In any one individual, as a result of injury, musculoskeletal asymmetry or inappropriate training, the ability to initiate and complete a reaction movement sequence may vary depending on the required movement direction. Comparing the specific movement vectors between the left and the right can quantify any deficits such that appropriate rehabilitation and/or training programs can be developed, progressed and monitored for effectiveness. For orthopedic rehabilitation applications, it is particularly important that the system allow reaction movement challenges to be controlled in both timing and distance to stay within prescribed limits of musculoskeletal stress.

For the testing method to be valid, objective and meaningful, the complete reaction movement sequence requires visual movement cues that appear in a realistic spatial representation and that clearly specify the required functional response. It is essential that the timing of each visual movement cue and/or the functional response specified be unpredictable to the individual being tested. Also the movement area must be of sufficient size to allow replication of relevant movements.

Certain critical moments within the reaction movement sequence cannot be discerned visually. Accurate measurement of the individual components of the reaction movement sequence requires a system capable of detecting minute loading changes in the movement area.

Another requirement for accuracy is the capability to reliably locate a subject's body center of gravity in order to measure movement distances and calculate movement speed. Previous technologies rely simply on detecting any contact with a target position. Merely contacting a position cannot be interpreted as effective movement of full body mass to that position. In the measurement of short distance movements, in particular, the error inherent in this method becomes so great that it may not be possible to distinguish reliably between world class and average performances. Furthermore, this method allows a subject, particularly one with long limbs, to cheat the test. To address this problem, means must be provided to insure that the subject starts and finishes at known points, i.e. that his center of gravity is accurately and consistently located at the beginning point and ending point of each movement. This invention accomplishes this requirement by requiring bilateral foot contact on two spaced positions that confine the distance variable yet still allow an appropriate functional response.

Various approaches have been suggested for assessing athletic movement and performance. None, however, have addressed and fulfilled the requirements for validly, objectively and meaningfully testing the complete reaction movement sequence. Elstein et. al. U.S. Pat. No. 4,702,475 discloses a rectangular exercise mat having marked pressure sensitive response areas around the perimeter. In response to a light prompt, the participant moves to a new response area thereby executing a directed movement pattern. The response areas are coupled to pressure sensitive binary switches. The system measures the time period from the prompt to the touching of the designated response area thereby activating the switch. The system does not measure reaction time from the appearance of the prompt to the beginning of change in loading that initiates the takeoff movement. Nor does the system measure contraction time from initial change in loading to lift off or the transit time from change in loading to full contact at the response area. Further, it does not measure the stabilization time from contact at the response area until a stable stance is achieved.

Yang U.S. Pat. No. 4,627,620 discloses an apparatus for measuring reflex, speed and accuracy wherein multiple targets are spread around the participant. The targets are prompted acoustically or visually and directing the participant move to and manually strike the target. A timer is activated at the prompt and deactivated at the strike by a binary switch. The time interval between the prompt and the strike is measured and displayed. The system does not and cannot measure reaction time, contraction time, transit time or stabilization time as described above.

Williams U.S. Pat. No. 4,645,458 discloses a training system wherein a player responds to a light prompt to leave a starting point and go to a first reaction point. The player is timed over the distance. At the first reaction point, a second light prompt directs the player to a second reaction point. The player is timed from the starting point to the second reaction point. As in the aforementioned prior approaches, the system does not measure reaction time, contraction time, transit time or stabilization time.

Alton U.S. Pat. No. 3,024,020 discloses an apparatus for testing agility wherein a floor platform has a geometric pattern of foot activated switches. A light display includes lamps arranged in a pattern similar to the floor platform. A selector box activates the lights to indicate a subsequent foot placement for the player. When the player attains that placement the lights are extinguished and another light set activated. The pace can be manually or automatically controlled through a predetermined movement path. The apparatus, while providing a sequenced movement path does not provide reaction time, contraction time, transit time or stabilization time.

Bigelow U.S. Pat. No. 4,534,557 discloses a reaction time and applied force feedback training system wherein a stimulus indicator, associated with a plurality of training devices, is energized to provide a signal to which the player responds by striking the training device. The system displays the time from the stimulus to the striking and the magnitude of the applied force. The system does not provide reaction time, contraction time, transit time or stabilization time.

Various video game formats have used a playing platform containing an array or pressure actuated switches. In response to character dramatization on a video screen, the player alters foot movement pace or changes direction in accordance with game rules. As in the aforementioned approaches, the binary switching does not fulfill the requirements for reaction movement sequence measurement.

In view of the foregoing limitations, it will be appreciated that the prior approaches, while providing stimulus prompted movement and indicia of performance, do not provide systems for testing and training of the important parameters of reaction movement sequence allowing assessing of performance and progress for relevant training and rehabilitation movements.

BRIEF SUMMARY OF THE INVENTION

The present invention provides an interactive reaction movement sequence testing and training system validly, credibly and accurately directing relevant reaction movement sequences under controlled conditions to measure reaction time, ground force time, transit time, stabilization time and stability index. The system employs a test field incorporating geometrically arrayed sensing pads or targets which generate analog signals responsive to minute changes in load or movement to provide signal information indicative of the reaction movement sequence parameters. The sensing targets are located in the test field in a converging radial array such that, from target to target, controlled lateral, forward, backward and diagonal movement patterns are prescribed. The signals are processed by a microprocessor for determining the parameters. A video screen coupled to the microprocessor displays a field graphically replicating the test field and targets. Responsive to participant movement, the video screen displays a visual prompt or cue to direct movement from a current position or target, presently occupied by the subject, to a subsequent position or target, thereby defining one leg of a routine or movement course. The signal generated at the current target from initiation of the prompt to initial movement provides information for determination of the reaction time. The signal generated at the current target from change in loading until generating sufficient force corresponding to lift-off from the initial weight bearing position on the current target provides the information for determining the ground force time. In conjunction with the signals from the subsequent target, the time interval from the change in loading until loading at the subsequent target corresponding to full contact therewith provides the information for determining transit time. At the subsequent target, the signals from the full contact determination until attaining movement corresponding to a stable stance provides information for determining stabilization time. This is achieved by determining when the analog signal, which varies with amplitude (force) and time, does not exceed a predetermined amplitude for a predetermined time interval.

The large number of possible movements, the visual specificity of movement cues and the focal range over which these cues can appear insure a lack of predictability that requires the subject to make true reaction movements. These reaction movements include perception and interpretation of the cue, the decisions on movement pattern and direction. Incorporation of these factors results in completely different and more realistic visual, neurophysiological and biomechanical challenges than previously available technologies that rely on pre-planned movements executed in response to non-specific starting cues which appear predictably in a focused location and no head tracking is required, inasmuch as the eye does not have to scan the horizon searching for cues.

BRIEF DESCRIPTION OF THE DRAWINGS

The above and other features and advantages of the present invention will become apparent upon reading the following detailed description of the preferred embodiments taken in conjunction with the accompanying drawings in which:

FIG. 5 is a top view of another embodiment of the sensor pad;

FIG. 6 is a cross sectional view taken along line 6—6 of FIG. 5;

FIG. 9 is a force curve for a person jumping on the sensor pad of FIG. 5;

FIG. 11 is a view of the summary video display for a testing and training session;

FIG. 12 is a top view of an embodiment of the sensor pad set;

FIG. 13 is an enlarged cross sectional view taken along line 13—13 in FIG. 12;

FIG. 14 is a representative waveform for the analog signal from a paired pad set;

FIG. 17 is a representative waveform for the analog signal to the convertor;

DETAILED DESCRIPTION OF THE PREFERRED EMBODIMENTS

Figure 1:
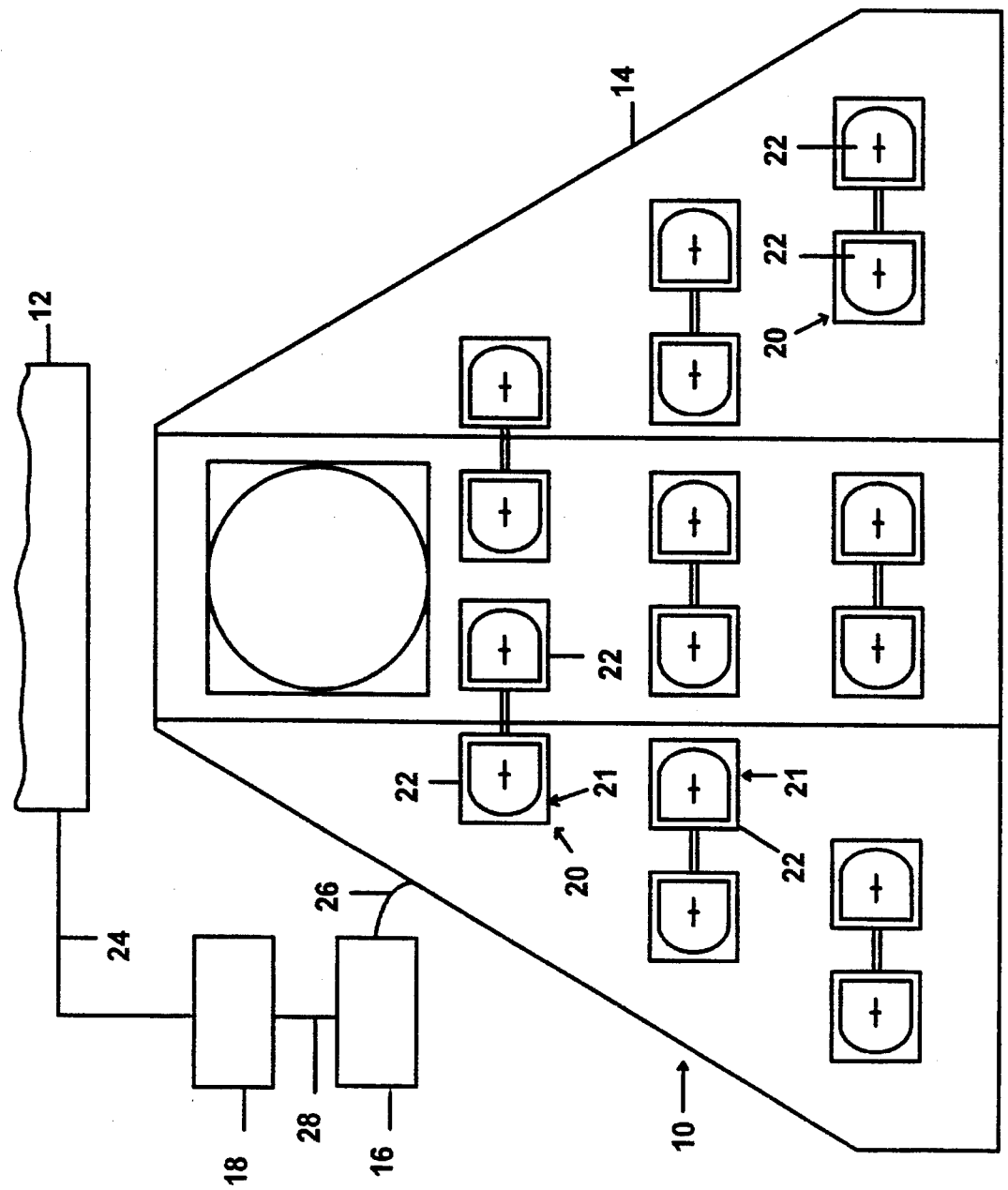
FIG. 1 is a top schematic view of a testing and training system in accordance with a preferred embodiment of the invention.

Referring to FIG. 1, there is shown a reaction movement sequence testing and training system 10 for directing and assessing leg movement performance of a user, player or subject. The system 10 comprises a video monitor 12, a test or playing field 14, a data acquisition module 16 and a graphics computer or microprocessor 18. The test field 14 includes a plurality of intercept targets or positions 20, each of which comprises and is defined by a pair of laterally spaced pad assemblies 21 having contrastingly colored sensor pads 22. As illustrated, there are eight intercept positions and sixteen sensor pads. However it will be appreciated that other combinations of positions and configurations may also be utilized.

The intercept positions 20 are geometrically oriented to locate a subject standing on the pads frontally facing the video monitor 12. The intercept positions 20 are arrayed on the field 14 to provide predetermined spatial relationships between positions which are reachable by singular or multiple lateral, forward and backward movements in a reaction movement sequence. As described in greater detail below, the pads 22 are provided with perimeter mounted analog sensors which provide an output signal in accordance with changes in loading on the pads.

The microprocessor 18 is operatively coupled to the video monitor 12 by a cable 24 and generates on the monitor screen a visual replication of the test field 14. The microprocessor 18 in addition generates a visual cue on the screen of the test field at a target intercept position corresponding to an intercept position different from the current intercept position of the subject. The module 16 receives the signals from the sensors at the pads 22 through a cable 26 and transmits to the microprocessor 18 through cable 28. As described below, the module and the microprocessor 18 determine (1) the time interval from the visual cue until change in loading or commencement of movement by the subject for exiting the current intercept position, i.e. reaction time, (2) the time interval from commencement of movement until the subject reaches the next intercept position, i.e. transit time, and (3) the time interval until the subject reaches predetermined stability on the intercept position, i.e. stabilization time. Additionally, the time interval from commencement of movement to takeoff from the pads, i.e. the ground force time, can be determined. When the subject reaches the next intercept position, subsequent visual cues are generated on the screen of the monitor 12 in a nonpredicatable fashion as to timing and prescribing a course of subject movement between the current intercept position and subsequent intercept positions. At the end of the training and testing session, based on the timing intervals, information is graphically presented on the screen related to the timing intervals.

The above system, more particularly, can analyze and quantify performance by determining certain leg movement parameters of the reaction movement sequence of a subject, moving on the field. By determining the current position of the player on the field and directing the player through visual cues on the screen to another position on the field, the time interval between the cue and the commencement of movement denoted by a change in loading, reaction time, can be determined. Further, by determining the time interval between the change in loading and departure from the pads, ground force time can be determined. Moreover, by determining the time interval between the change in loading and arrival at another position, the transit time and the transit speed may be determined. Still further by determining the time interval between the arrival at next position and the subject having achieved predetermined stability, stabilization time can be determined. At the conclusion of the programmed course, information is displayed on the screen permitting an analysis of the reaction movement sequence as to problems, improvement and actual performance. For each distinct pattern, forward, backward or lateral, a comparison between left movement and right movement activity may be displayed and compared to note any deficiencies based on averaged data.

Figure 2:
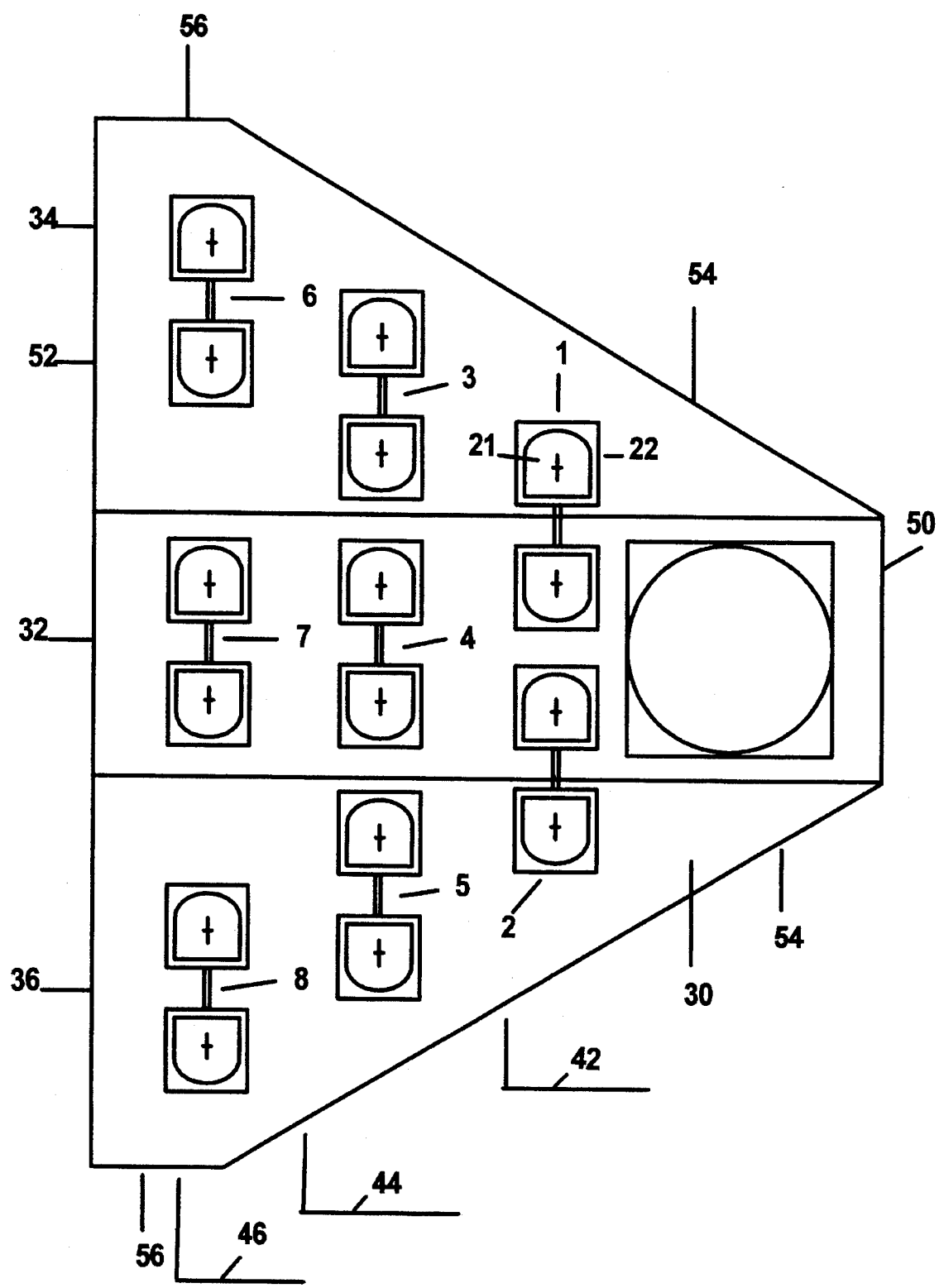
FIG. 2 is a top view of the test field for the testing and training system.

Referring to FIG. 2, the test field 14 comprises a horizontal platform 30 having the eight intercept positions 20, numbered 1 through 8, defined by the sets of sensor pads 22. The top surfaces of the pads 22 are flush with the top surface of the platform 30. The intercept positions 20 are arrayed on the platform 30 along three radial columns 32, 34, 36 converging at a focal point in a plane at approximately the front surface of the video monitor. The pads 22 are located in three rows 42, 44, 46 spaced transversely from the monitor. Column 32 is on the centerline of the monitor and columns 34, 36 are uniformly angularly spaced with respect to the center column 32 at approximately 20° to 40°, preferably around 30°. Two pad sets are located on the outer columns 34, 36 in the front row 42. Three pad sets are located on each vector in the middle row 44. Three pad sets are located on each column in the back row 46. The rows are uniformly spaced fore and aft.

The platform 30 is a laterally truncated trapezoidal shape defined by a front wall 50 parallel to the monitor, a rear wall 52 parallel to the front wall 50, front side walls 54 parallel to the vectors 34, 36, and rear side walls 56 parallel to the center vector 32. The cable 26 shown in FIG. 1 from the pad sets are routed through channels or the like formed in the bottom surface of the platform. Inasmuch as there are practical restrictions on the size of the video screen and its distance from the field, locating the intercept positions on converging radials minimizes parallax and image distortion that might otherwise be experienced at the front corners of the screen. Also, the converging radial array insures that the subject stays within viewing angles that are not affected by the roll off of brightness inherent in current large screen projection systems.

The design and location of the intercept positions provides a training field providing six distinctly different movement categories in fifty six possible movement vectors at thirty different vector/distance challenges balanced between left movement vectors and right movement vectors.

The platform 30 and the pad assemblies 21 are preferably a resilient material, such as molded urethane or rubber. The top surface of the platform and pad assemblies may be smooth or textured if desired.

Figure 3:
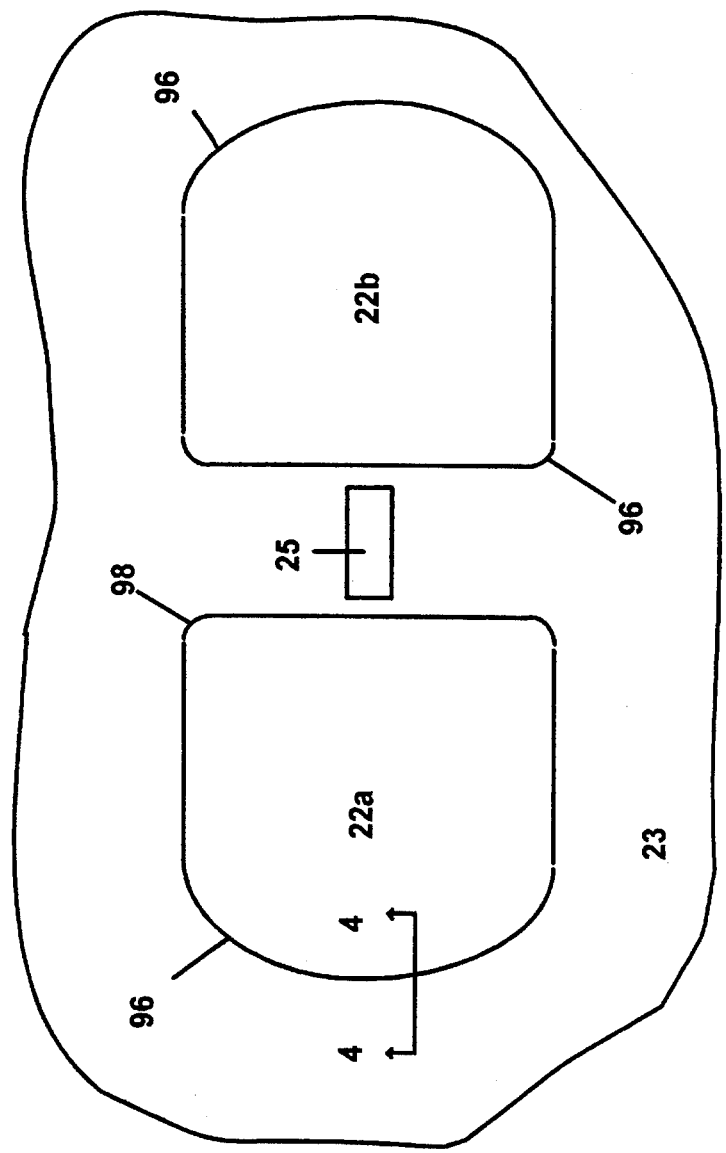
FIG. 3 is an enlarged fragmentary plan view of one embodiment of a sensor pad set.

To obtain accuracy in measuring the movement distances and calculating movement speed, the subject's body center of gravity must be accurately located. Merely detecting contact at an intercept position is not sufficient and cannot be necessarily interpreted as effective movement of full body mass to that position. Referring to FIG. 3, accuracy is provided in the present invention by providing two sensor pads, a left pad 22a and a right pad 22b, at each intercept position 20. The pads are laterally spaced by a center bridge section 23 of the platform 30 such that center to center distance between the pads provides for a normal relevant stance by the subject. The section 23 is provided with a removable cover plate 25 for accessing the electrical wiring connection for the pads. Measurement of body weight to confirm arrival at the target platform could be accomplished with a single conventional force platform.

Figure 4:
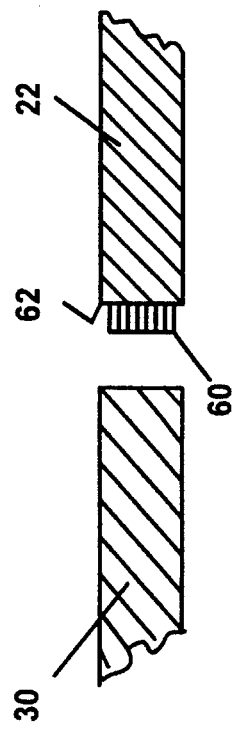
FIG. 4 is an enlarged cross sectional view taken along line 4—4 in FIG. 3.

Referring to FIG. 4, each pad 22 has a piezoelectric transducer 60 mounted on the perimeter side wall 62 thereof which generates an analog signal in response to changes in loading on their top surface. The surrounding area of the platform 30 is not force measuring, serving primarily to provide a movement surface that is horizontally coextensive and flush with the pads. This helps to prevent tripping and provides proper texture and distinguishing markings for the field. The field is sufficiently large to allow for movement distances that replicate actual sports movements, ranging between approximately 30 inches to 10 feet. Referring to FIGS. 5 and 6, a representative sensor pad 70 comprises a cylindrical pad 72 having a flexible polymeric piezoelectric transducer sensor strip 73 mechanically or adhesively coupled to the side wall 74 of the pad 72. The strip 73 has output leads 75 and 76 operatively connected to an output device 78. The pad 70 measures, accurately and uniformly, loading changes caused by movement of location 77, illustrated in dashed lines, randomly impacting or moving on a portion of the front surface 79 of the pad 70 as detected by the strip 73 and outputed to the device 78.

The piezoelectric material referred to with respect to the various embodiments described herein is preferably a polarized polyvinylidene fluoride (PVDF) film sandwiched between metallized layers of electrically conductive metal. This multilayered material is marketed under the trademark KYNAR by the Pennwalt Corporation, 900 First Avenue, King of Prussia, Pa.

Figures 7, 8:
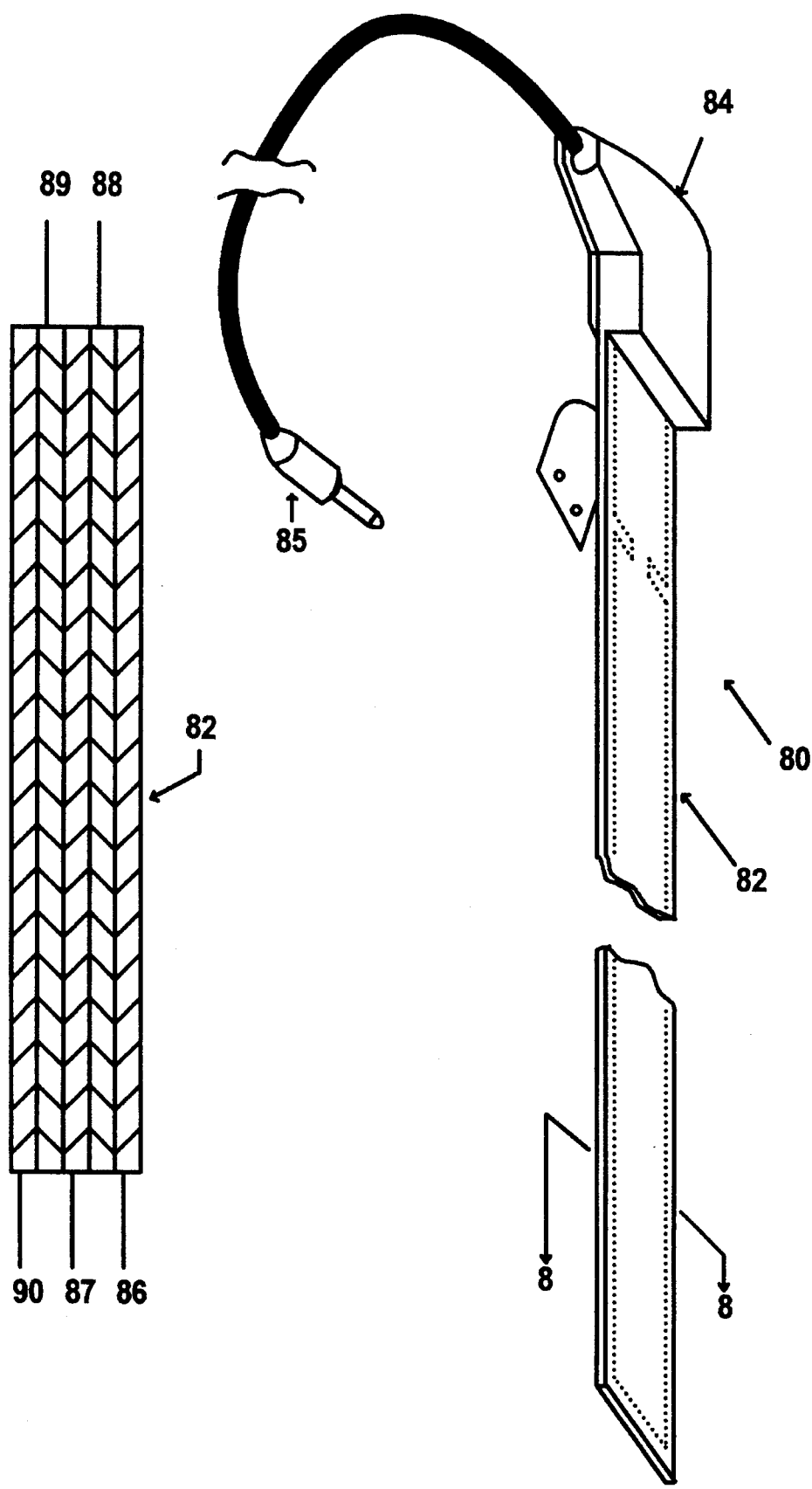
FIG. 7 is a perspective view of a piezoelectric sensor assembly.
FIG. 8 is an enlarged cross sectional view taken along line 8—8 in FIG. 7.

As shown in FIG. 7, a piezoelectric sensor assembly 80 comprises an elongate transducer strip 82 electrically coupled to a cable 83 at a connector housing 84. The cable 83 terminates with a molded connector plug 85 adapted to be connected to the output device, referenced above. As shown in FIG. 8, the transducer sensor strip 82 is a multilayer laminate comprising an outer Mylar layer 86, a middle polymeric piezoelectric sheet 87 having metallized coatings 88 and 89 on either side thereof, and an inner Mylar layer 90. The layers 86 and 90 are adhesively attached to the sheet 87. Additionally, the inner layer may be provided with an adhesive layer for coupling attachment to the pad, with the adhesive protected prior to installation by peel back release paper. As used in the embodiments described herein, the piezoelectric film is approximately 28 microns in thickness, and the opposed metallized layers are silver of about 0.1 microns in thickness.

The pad is preferably formed of a homogeneous material of substantially uniform elastic constant. While the pad may be formed of high elastic constant materials such as metals, woods, and hard plastics, it is generally preferred to use polymeric materials, such as rubber, softer plastics, polymer foams and like materials having an elastic constant similar to the film strip and that are resilient and locally deformable to aid in wave energy propagation to the transducer strip.

Excellent coupling has been obtained through adhesive attachment using pressure sensitive adhesive supplied by 3M, such as Product No. Y-9485 for the polymeric foam pad, and Product No 950 for solid rubber pads. The strip so coupled has material properties well matched to the pad and provides high piezoelectric sensitivity, low mechanical and acoustic impedance to produce accurate, ascertainable throughout a broad range of loadings. Moreover, because of the toughness and flexibility of the materials, the strip is not subject to breakage or loss of dipolar properties when subjected to mechanical impact in velocity measuring embodiments described below.

FIG. 9 shows a typical force curve generated by person on the platform during the course of a jump from and onto the pad. Therein, point 91 represents the time or start of the jumping activity, point 92 the time of take off and point 93 the time of landing. Eccentric time equals point 90a less point 91, and concentric time equals point 92 less point 91a, measurements of both components of the jump. The time interval between points 91 and 92 represents the coupling time of the jump. It will be noted that the coupling time is represented by two distinct phases. First, an eccentric phase as the jumper is lowering the body center of mass preparatory to jumping and a concentric phase as power is expended in jumping followed by a decreasing force as the weight is removed from the platform terminating with a minimum force indicative of the take off. The time interval between take off and landing is the jump or air time and is one parameter for indicating vertical rise of the center of mass, or jump height. Alternatively the slope of the curve between points is a function of take off velocity from which vertical rise may also be determined. The power expended in the jump may also be derived as a function of body weight. Thus the force over the concentric phase or the force over the landing phase may be used as a function of body weight in power determination. For such devices, it is preferred to use a high durometer rubber pad for the platform which is resilient and locally deformable. Suitable examples of such material are 50 to 70 durometer synthetic rubber compounds.

For use in the present invention for a testing and training system, as shown in FIG. 3, each set of pads in this embodiment is Generally elliptically shaped in overall plan view configuration. Each pad 22 has large radius outer corners 96 and small radius inner corners 98. The overall shape insures that the subjects center of gravity is located within a sufficiently confined area to allow accurate distance measurements in movements between intercept positions. The set accommodates a normal lateral stance, ranging typically from about 22" to 40" on the X axis, while confining fore and aft position, about 12" to 20" on the Y axis. By having the subject start and finish at these known confined points, the body center of gravity is accurately and consistently located at the starting and ending point of each reaction movement sequence.

Uniform geometric shapes, such as squares or circles, can also be used.

Figure 10:
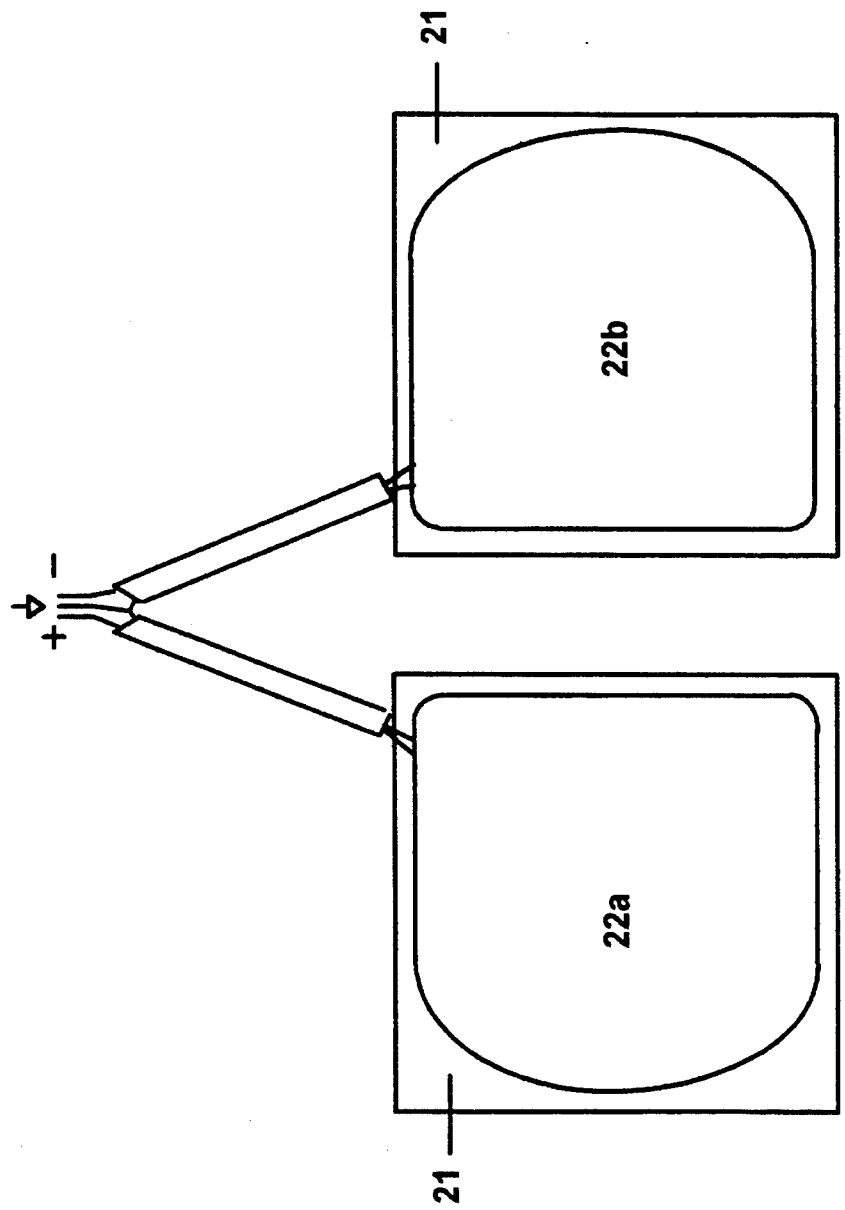
FIG. 10 is an electrical schematic for the sensor pads.

Referring to FIG. 10, there is shown the schematic diagram for one method for transmitting the signals from a pad set consisting of a left pad 22a and a right pad 22b. The positive lead from the piezoelectric sensor of the right pad 22b is connected to the negative lead of the piezoelectric sensor of the left pad 22a and grounded. The positive lead from the piezoelectric sensor of the left pad 22a and the negative lead of the piezoelectric sensor on right pad 22b transmit the charge to charge the module 16. Accordingly, changes in loading or force applied at the left pad 22a will be transmitted as positive charge signals whereas changes in loading or force applied at the right pad 22b will be transmitted as a negative charge signals. Thus the signals from the pad set to the data acquisition module 16 can be processed with a single amplifier while discriminating between events on the individual pads.

Referring to FIGS. 12 and 13, the sensor pads are incorporated in a rectangular unitized pad assembly 21 slidably received within rectangular apertures in the platform 30 defined by inwardly facing cylindrical wall 102 thereof in locations corresponding to the intercept positions 20. The pad assembly 21 has an outer perimeter wall 104 corresponding to the wall 102 and insertable therewithin. The pad assembly 21 is molded as a single piece and has a continuous downwardly opening narrow groove 106 formed in the lower surface thereof defining inwardly the sensor pad 22 integrally connected to a surrounding frame 108 by a thin continuous web or membrane 109. The piezoelectric sensors 70 are secured to the peripheral walls of the pads beneath the webs 109. The web 109 is relatively thin and effectively prevents force transmission from the frame 108 to the pads and sensors.

Figure 36:
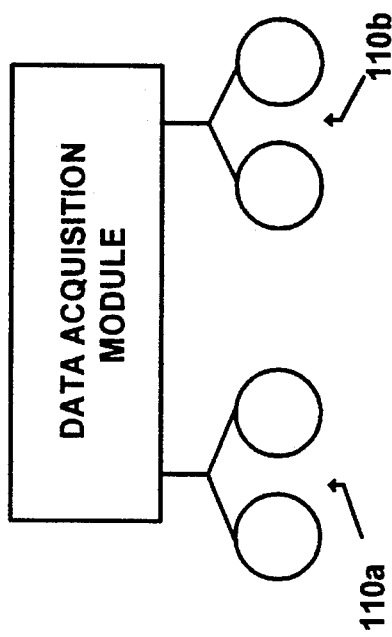
FIG. 36 is a schematic diagram of the connection between two groups of paired platforms to the data acquisition module.

Referring to FIG. 14, a representative wave form for the analog signals transmitted from two groups of paired platforms, $110_a$ and $110_b$, FIG. 36, to the data acquisition module is shown for a subject at rest at a first intercept position, IP-1. Referring to FIG. 36, the paired platforms, $110_a$ and $110_b$ are placed physically close to each other such that the subject's preparatory stance is achieved by contacting both pads located at a distance approximately a shoulder width apart.

The subject receives a visual cue directing movement to a second intercept position, IP-2, and executes a reaction movement sequence to that intercept position IP-2. During time interval, $t_p$, the subject has a stable stance represented by low level, low frequency fluctuations. The visual cue is initiated at timing point 110. At timing point 112, one leg begins a change in loading initiating a voltage peak. The time interval between timing points 110 and 112, $t_r$, represents the aforementioned reaction time.

At timing point 114, the second leg begins change in loading denoted by a reverse polarity voltage peak. At timing point 116, where the voltage returns to zero, the subject has exited the first intercept position. The time interval between timing points 112 and 116, $t_c$, represents the aforementioned contraction time.

At timing point 118, the subject has arrived on one foot at the second intercept position, IP-2, as indicated by the initiating of a reverse polarity voltage peak. The second foot contacts the other pad at timing point 120 as signaled by a positive voltage peak. The time interval between timing points 112 and 120, $t_t$, represents the aforementioned transit time. Based on the distance between the intercept positions, the aforementioned transit speed can be determined.

After full contact at the second intercept position, IP-2, a period of weight shifts between the pads occurs indicated by large amplitude voltage oscillations which dampen in amplitude and frequency. The amplitude reaches a predetermined value, empirically defining balance, at timing point 122. The time interval between timing points 120 and 122, $t_s$, represents the aforementioned stabilization time. The session continues with a second visual cue at timing point 124.

Figure 15:
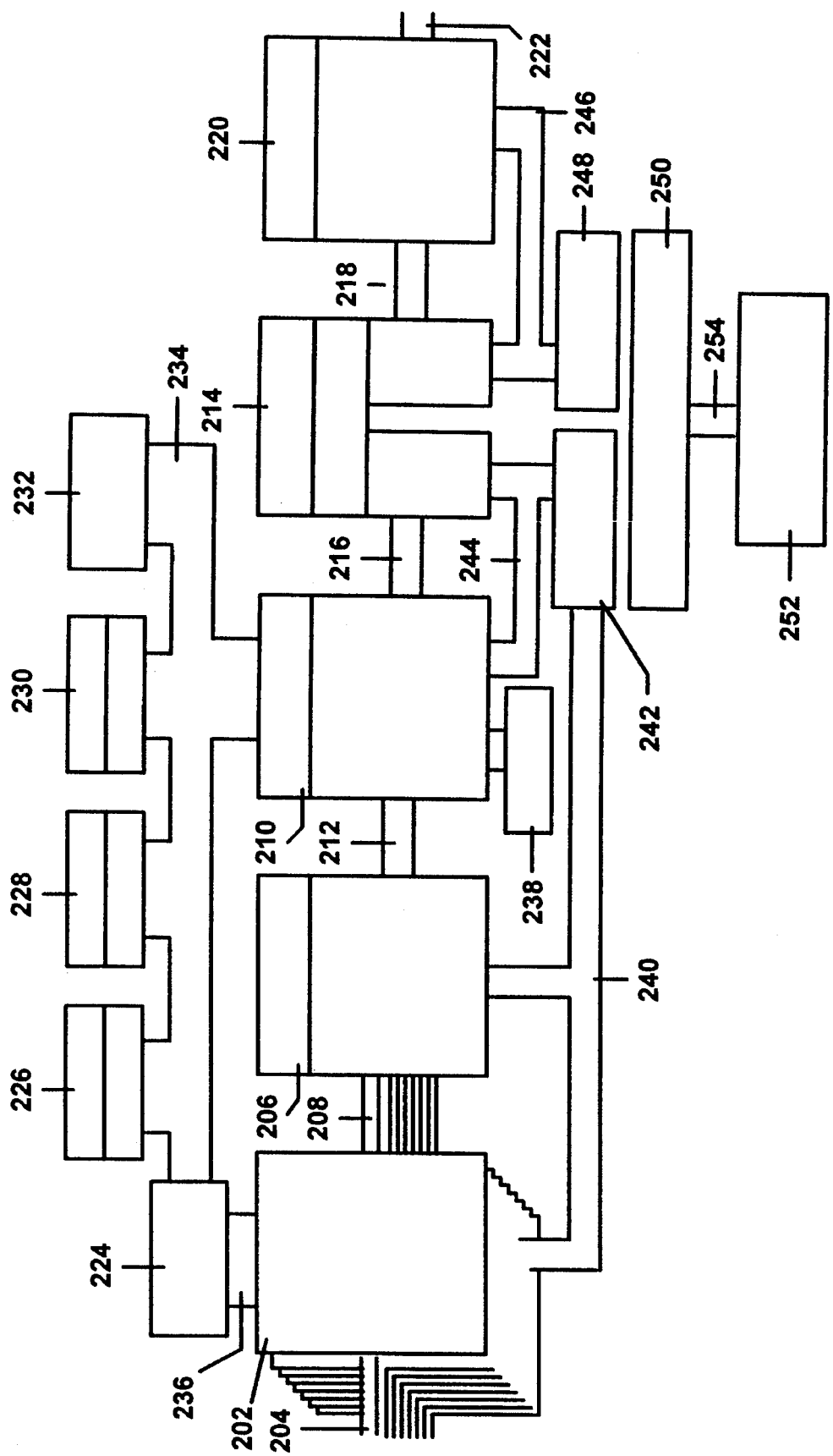
FIG. 15 is a schematic diagram for the data acquisition module.

Referring to FIG. 15, there is shown a schematic diagram for the data acquisition module 16 for the the system 10. The module 16 receives the analog signals from the pads and converts the signal to digital information which is transmitted to the microprocessor 18. More particularly, the module 16 includes eight charge amplifiers 202, however, it will be appreciated that one amplifier per pad can also be used to eliminate pairing as described below. Each amplifier 202 receives the analog signals from the pads along lines 204, an analog/digital converter 206, which receives the integrated signals from the amplifiers 202 along lines 208, a microcontroller 210, which receives a digitized multiplexed signal from the converter 206 along lines 212, an isolation optocoupler 214 having an input which receives the processed signal from the controller along lines 216 and an output which transmits the processed signal along lines 218 to a driver/receivers 220, which transmits a RS-232 voltage compatible signal to the microprocessor 18 along lines 222. The optocoupler 214 isolates the microprocessor 20 from the upstream components. I/O decoders 224, EEPROM 226, data buffer 228, firmware EPROM 230 and external expansion bus 232 are interconnected to the microcontroller 110 by address/data bus 234. The decoders 224 are connected to the amplifiers 202 along lines 236. The microcontroller 210 is provided with a reset 238 for maintaining operation during momentary power interruption.

The amplifiers 202 and converter 206 are connected by analog power bus 240 to positive/negative post regulator 242. The microcontroller 210 and the input of the optocoupler 214 are connected by digital power bus 244 to the regulator 242. The output of the optocoupler 214 and the driver receiver 220 are connected by digital power bus 246 to a positive post regulator 248. The regulators 242 and 248 are conventionally connected to a three way power isolation transformer 250 which is connected an AC/DC plug-in wall transformer 252 along lines 254 for connection to a suitable external power source, not shown.

Figure 16:
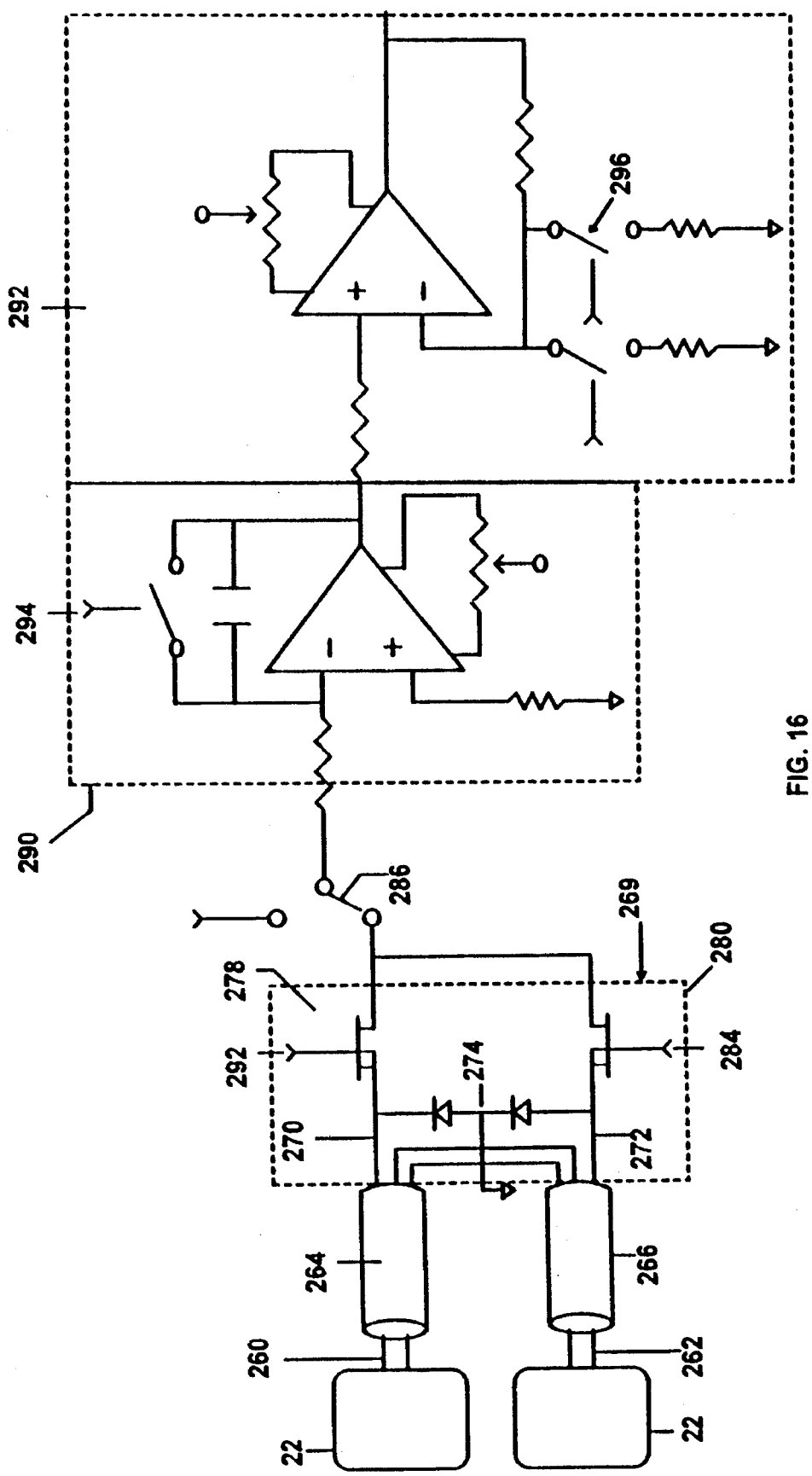
FIG. 16 is a circuit diagram for the amplifiers.

Referring to FIG. 16, each of the amplifiers 202 is multistaged and integrate the differential analog signal received from the sensors to provide linear outputs to the converter 206. More particularly, the output leads 260 and 262 from the pads are respectively connected to shielded cables 264 and 266. At the module 16, the negative lead from one pad is interconnected with the positive lead from the other pad and grounded. At the peak detection stage 269, the positive lead 270 from cable 264 and the negative lead 272 from cable 266. Diodes 274 protect the MOSFETs from over-voltage stress. Lead 270 is connected to the source of MOSFET 278. Lead 272 is connected to the source of MOSFET 280. The gates 282, 284 of the MOSFETs are connected to and controlled by the firmware and routed through a DPDT relay 286 controlled by the microprocessor 18. The relay connects the drains of MOSFETs to an integrator 290. The integrator 290 is connected to a amplifier 292. In the other condition of the relay 286, a square wave calibration signal derived from the microcontroller may be applied to the integrator 290 and amplifier 292 to permit calibration of gain and drift stability. The integrator 290 and amplifier 292 are provided with input/offset voltage adjustment. A reset switch 294 controlled by the microcontroller resets the integrator to zero voltage. The non-inverting amplifiers 292 are provided with adjustable gain switches 296 to permit sensitivity adjustment. By providing +5/−5 volt biasing of the MOSFETS, a peak detection and hold function is provided that allows greater versatility for triggered data interpretation.

Referring to FIG. 17, there is shown a representative wave form for the analog signals presented to the convertor from the amplifiers for a subject at rest at a first intercept position, IP-1. First, the MOSFETs are enabled to set peak detection mode. The subject receives a visual cue directing movement to a second intercept position, IP-2, and executes a reaction movement sequence to intercept position IP-2. During time interval, $t_p$, the subject has a stable stance. The visual cue is initiated at timing point 300. At timing point 302, one leg begins a change in loading initiating a voltage peak. The time interval between timing points 300 and 302, $t_r$, represents the aforementioned reaction time.

At timing point 304, the second leg begins change in loading denoted by a reverse polarity voltage peak. At timing point 306, where the voltage returns within a threshold voltage representing takeoff, the amplifiers are reset, and the subject has exited the first intercept position. The time interval between timing points 302 and 306, $t_c$, represents the aforementioned contraction time.

At timing point 308, the subject has arrived the one foot at the second intercept position, IP-2, as indicated by the initiating of a reverse polarity voltage peak. The amplifiers are reset bringing the signal to zero. The second foot contacts the other pad at timing point 310 as signaled by a positive voltage rise. The amplifier is reset and the MOSFET's are disabled. The time interval between timing points 310 and 302, $t_t$, represents the aforementioned transit time. Based on the distance between the intercept positions, the aforementioned transit speed can be determined.

After both legs contact at the second intercept position, IP-2, a period of weight shifts between the pads occurs indicated by large amplitude voltage oscillations which dampen in amplitude and frequency. The amplitude reaches a predetermined value, empirically defining balance, at timing point 312. The time interval between timing points 310 and 312, $t_s$, represents the aforementioned stabilization time.

The converter 206 is a 12 bit analog/digital design having an eight channel multiplexed analog input bus and internal sample hold circuitry. The converter provides eight channel digitizing and multiplexing of the analog information from the amplifiers 202 up to a sampling rate of 300 HZ per channel. The converter has a programmable configuration register for span, data size, and bipolar inputs. A suitable converter is available as product no. LT 1290 manufactured by Linear Technology.

The microcontroller 210 is an eight bit design operating at 11 MHz with internal serial communication registers and an 8 bit I/O ports. A suitable microcontroller is available as product no.80C31 manufactured by Signetics.

The optocoupler 214 provides for voltage isolation between the microcontroller 210 and the driver/receiver 220. A suitable optocoupler providing 500 volt isolation is available as product no. HPCL-2200 manufactured by Hewlet Packard.

The driver/receiver 220 level—shifts the incoming logical voltages to the appropriate voltage levels as required by the microprocessor. A suitable device is available as product no. LT-1080 manufactured by Linear Technology.

The decoders 224 are 48 bit I/O latches which are conditioned by the firmware 230 and the microprocessor for configuring the amplifiers for the various routines or programs for the system. Accordingly, the decoders 224, in a conventional manner, can regulate the gain, provide reset, provide peak detection, permit calibration signal injection, and like functions.

The EEPROM 226 is a voltage erasable programmable device which verifies the compatibility of the system hardware and software. A suitable device is a 1 Kbit EEPROM part available from Microchip.

The data buffer 228 accepts data from the microcontroller under conditions when the data transmission of the convertor exceeds the transaction capabilities of the microprocessor 18. A suitable device is a 32 Kbyte SRAM manufactured by Toshiba as Product No. TC 55257BPL.

The firmware 230 is an ultraviolet light erasable programmable device which interprets software commands, checks for program errors, and controls sampling and amplifier configuration. A suitable device is a 64 Kbyte EPROM manufactured by Intel as Product No. 27C512.

The expansion bus 232 is used for connecting peripheral devices to the module for handling routines not performed by those described herein.

The microprocessor for controlling and running the testing and training system is preferably a microcomputer. Suitable for use in the system is a Commodore Amiga 2000 personal computer using a Motorola 68000 chip having a 16/32 bit central processing unit, 1 MB RAM, multitasking operating system. For data entry, a keyboard or mouse may be used with a track ball being preferred for the on-screen running of the routines.

At the end of the testing/training session, information may be displayed on the video screen, in whole or in part, as representatively shown in FIG. 11. For a comprehensive movement skills analysis, the aforementioned timing parameters are displayed for left and right movements and summarized as forward, backward and lateral movements. Representatively, for forward movements, left and right, the reaction time, contraction time, transit speed based on microprocessor calculation based on transit time and movement distance, and stability time are displayed. Also displayed is the deficiency in movement between the strongest and weakest direction measurement. Based on the content of the session, the average results for the session are summarized.

For other routines, some or all of these measurements can be displayed as relevant for the content of the programmed session. An aerobic exercise routine in a preferred format would display the reaction time and transit speed between intercept positions for forward, backward and lateral movements. Total distance and calories burned may also be displayed.

For testing and training to be reliable, and therefore useful for comparing performance among different subjects or for detecting changes in a single subject's performance, the test method must allow sufficient repetitions of an entire range of reaction movement sequence directions and distances to be replicated without predictability of movement cues.

The possible movement paths for the illustrated test field are summarized in Table 1 below:

TABLE 1

| Movement | Path | Distance |
| --- | --- | --- |
| Forward | | |
| Right | 3 > 1, 6 > 3 | 36 |
| | 6 > 1 | 72 |
| | 7 > 2 | 65 |
| Left | 5 > 2, 8 > 5 | 36 |
| | 8 > 2 | 72 |
| | 7 > 1 | 65 |
| Straight | 7 > 4 | 31 |
| Backward | | |
| Right | 2 > 5, 5 > 8 | 36 |
| | 2 > 8 | 72 |
| | 1 > 7 | 65 |
| Left | 1 > 3, 3 > 6 | 36 |
| | 1 > 6 | 72 |
| | 2 > 7 | 65 |
| Straight | 4 > 7 | 31 |
| Lateral | | |
| Right | 1 > 2 | 42 |
| | 3 > 4, 4 > 5 | 39 |
| | 6 > 7, 7 > 8 | 57 |
| | 3 > 5 | 78 |
| | 6 > 8 | 114 |
| Left | 2 > 1 | 42 |
| | 4 > 3, 5 > 4 | 39 |
| | 7 > 6, 8 > 7 | 57 |
| | 5 > 3 | 78 |
| | 8 > 6 | 114 |
| Diagonal Forward | | |
| Right | 4 > 2 | 38 |
| | 7 > 5 | 50 |
| Left | 4 > 1 | 38 |
| | 7 > 3 | 50 |
| Backward | | |
| Right | 1 > 4 | 38 |
| | 3 > 7 | 50 |
| Left | 2 > 4 | 38 |
| | 5 > 7 | 50 |
| Pivot and Stride Forward | | |
| Right | 3 > 2 | 68 |
| | 6 > 2 | 99 |
| | 6 > 5 | 101 |
| | 6 > 4 | 65 |
| Left | 5 > 1 | 68 |
| | 8 > 1 | 99 |
| | 8 > 3 | 101 |
| | 8 > 4 | 65 |
| Backward | | |
| Right | 1 > 5 | 68 |
| | 1 > 8 | 99 |
| | 3 > 8 | 101 |
| | 4 > 8 | 65 |
| Left | 2 > 3 | 68 |
| | 2 > 6 | 99 |
| | 5 > 6 | 101 |
| | 4 > 6 | 65 |

This is achieved in the present invention by mixing the visual movement cues so that their order cannot be anticipated or memorized while, at the same time, insuring that all the same vector/distance movement combinations are included in the routine and that the physiological work requirements are equilibrated in repeated testing sessions.

More particularly, each session includes all the above movement paths. The paths are grouped into closed loop sets, wherein any starting point in the loop is the same as the finishing point for that loop. The starting point in the initial set may be selected or randomly generated. After completing the first set, the second set is randomly chosen from the remaining sets and the set is entered at a starting point the same as the finishing point for the previous set. The closed loop set sequencing reduces the computer processing task while insuring that the sequence generates such a substantial number of movement possibilities that memorization is not possible and the cues thus become non-predictable.

For instance, an eight platform system as described above could be structured in seven sets of an eight movement path loop. Each set is composed to provide a balance of movement directions and distances, such that each session, even if not fully completed, nonetheless provides balanced right and left moves. As programmed, no two sessions are identical. However, the content of the session is similar as to content of movements and challenges such that physiological demands are controlled and the results among individuals and associated progress over time are comparable.

Figure 18:
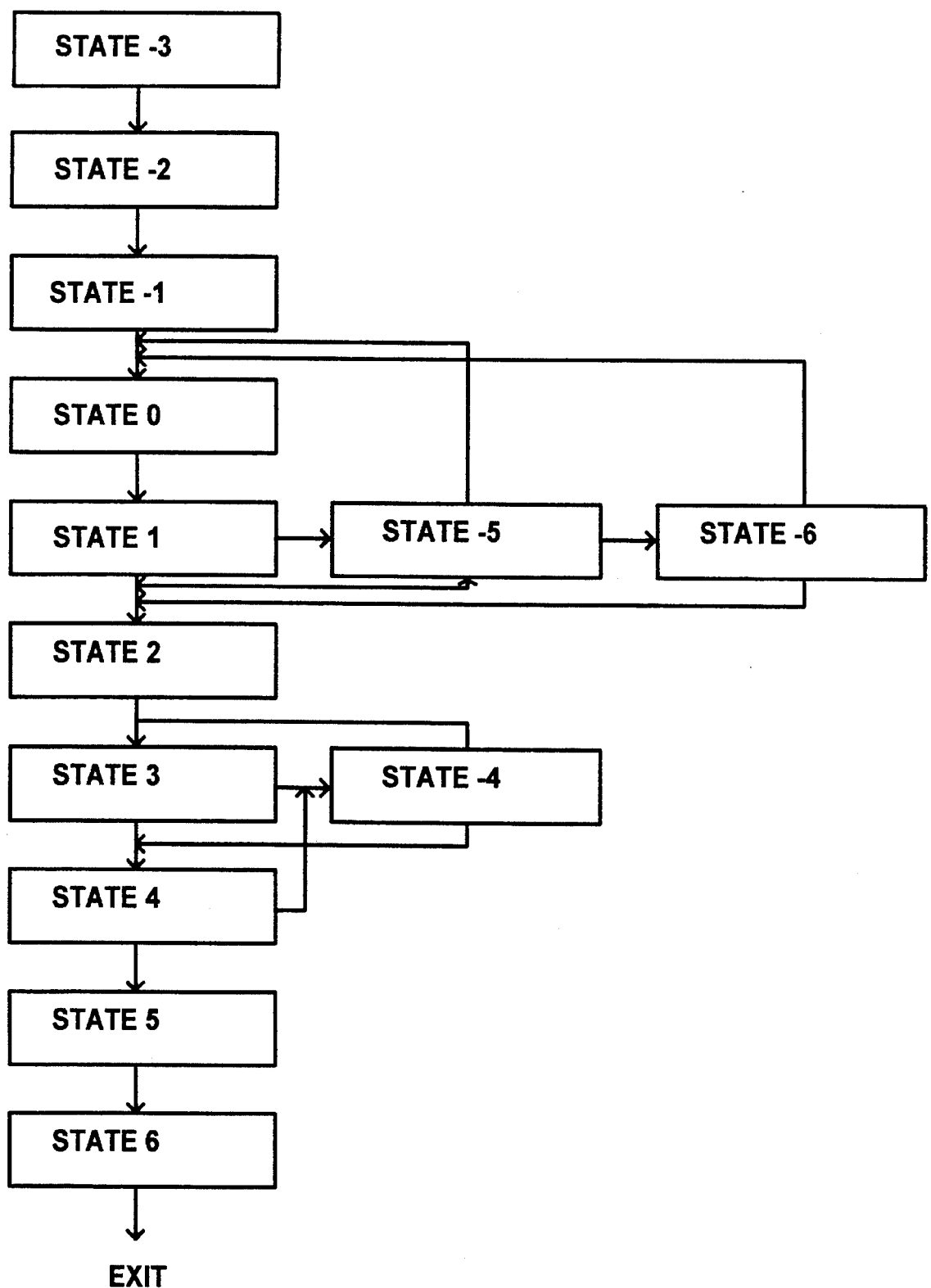
FIG. 18 is the state flow path for conducting a testing and training session.

The software for controlling the microprocessor in a test and training session for measuring the parameters of the reaction movement sequence is shown in FIG. 18. The running system exists in a loop of positive or active states. The positive states allow the system to know the current intercept position of the subject. The negative states are initialization steps or fault processing states.

A waiting period is provided in each state. Before incrementing to a new state, the system is conditioned to wait for a particular platform event or trigger. When the event is detected, the system performs an exiting routine and advances to a different state, determined by that event and its timing parameters. If the platform event is not detected, the system advances to a negative fault or exit state.

The hardware issues to the software a trigger message when a platform event occurs, and thereafter an exit message to indicate that the current state should be exited or incremented. As hereinafter described, the microprocessor can also make the exit decision.

The hardware monitors timing using what is hereinafter referred to as a "hardware interval timer". Each time a trigger message occurs, the microprocessor is given a timestamp or value from the microcontroller for the occurrence and the hardware interval timer is reset. Thus for each occurrence, the trigger message of the timer is the time interval elapsed since the last trigger timestamp was reported, the intercept-position, and the polarity of the trigger.

The microprocessor also operates asynchronous counters, referred to as "interval timer" and "stability interval timer".

The initial setup for the session consists of states -3 through -1. The testing and training loop consists of states 0 through 5. States -4, -5 and -6 are fault states where a subject performance error has occurred. State 6 is the final "session over" state where the session has concluded.

Figure 19:
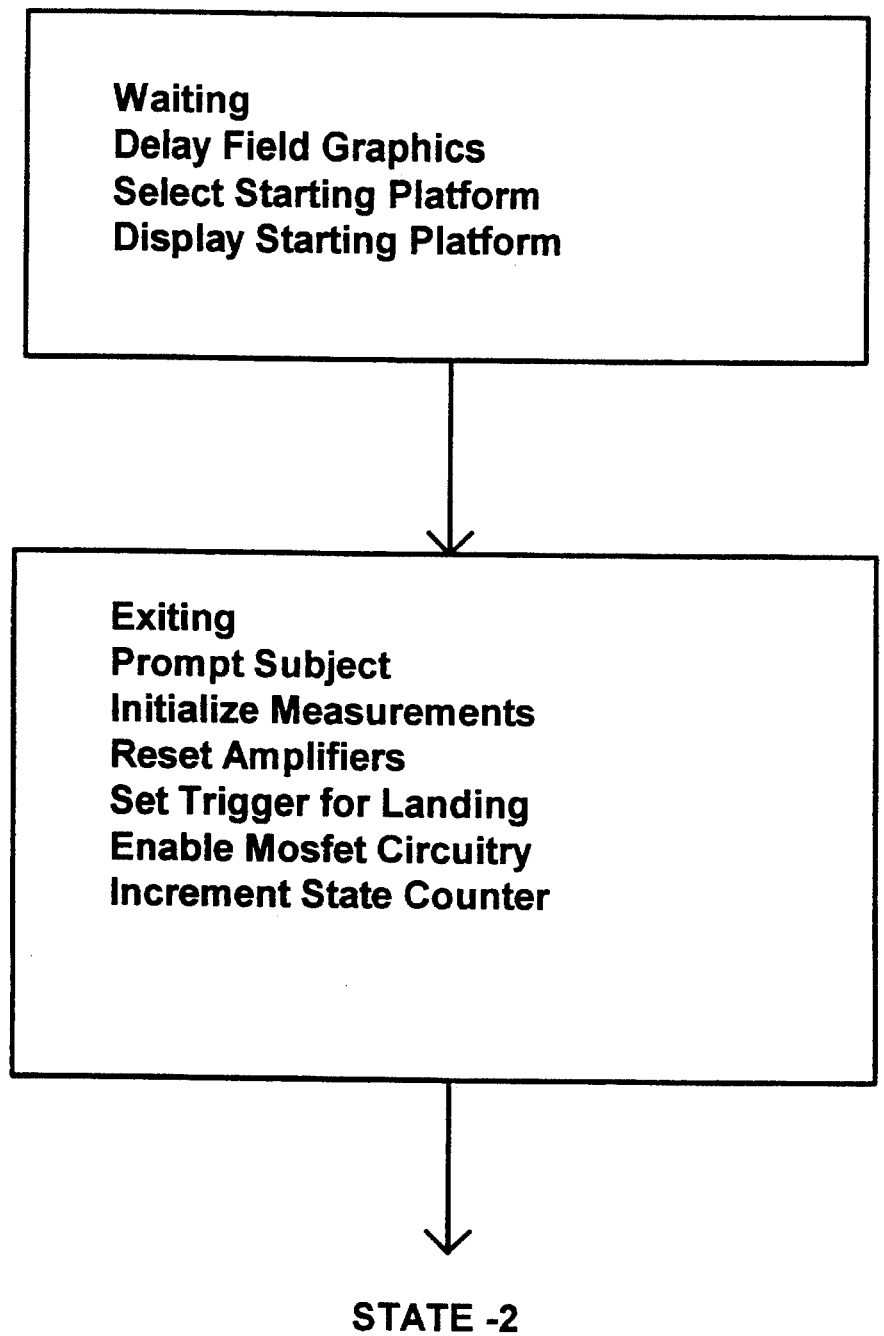
FIGS. 19 through 31 are operational block diagrams for the individual states.

Regarding the initial set up, as shown in FIG. 19, in state -3 or Start State, while waiting the field graphics are displayed on the monitor, an initial intercept position or initial platform is selected and displayed, and the subject is prompted to move to the initial platform. All measurements are initialized to zero and the interval timers are reset. Additionally, before awaiting arrival of the subject on the initial platform, the trigger is set for the the takeoff value, the MOSFETs are enabled and amplifiers at the initial platform are reset. Thereafter the state counter is incremented to enter State -2, the First Platform State.

Figure 20:
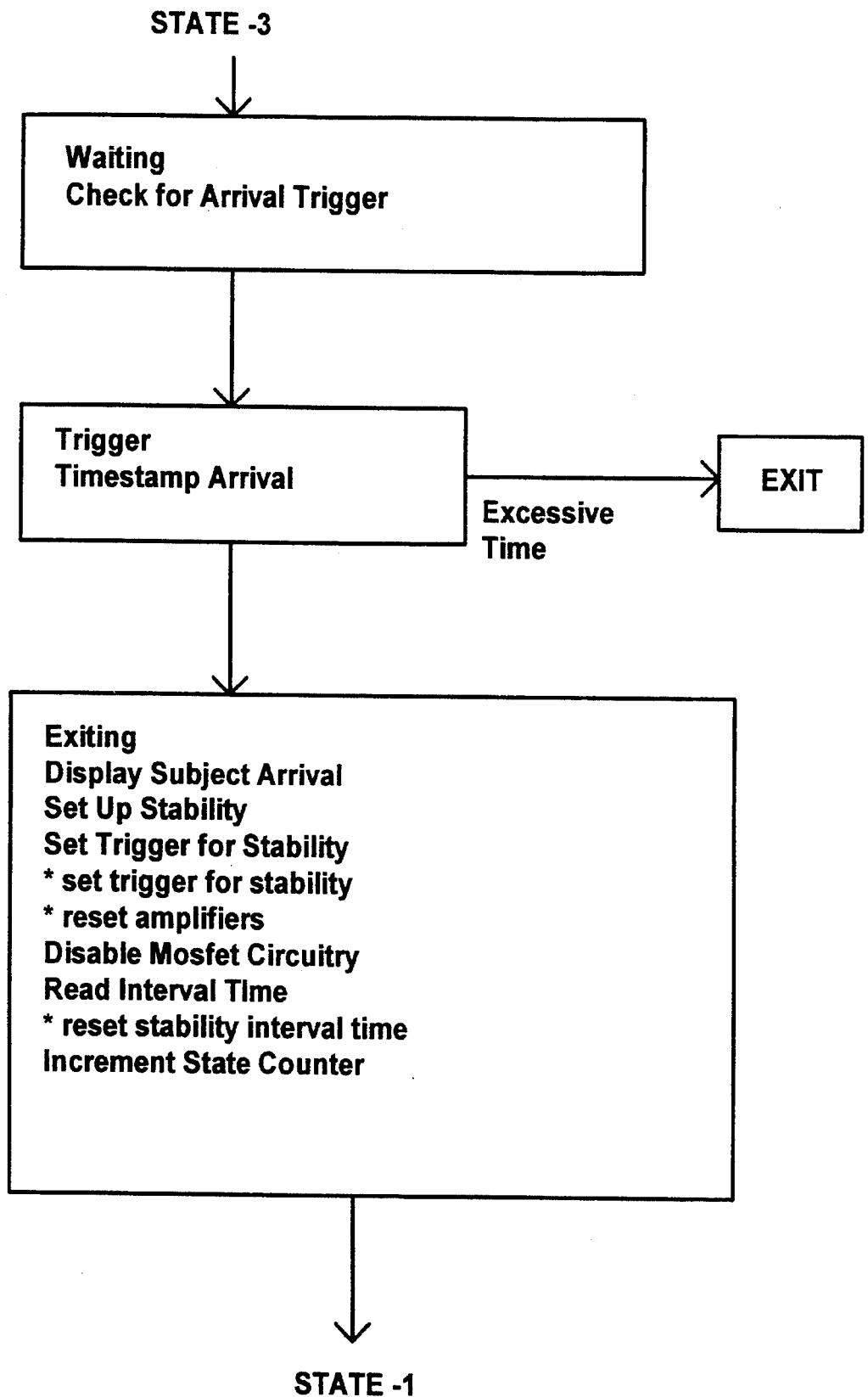

In State -2, as shown in FIG. 20, the system is awaiting arrival of the subject on the initial platform. If more than a predetermined time elapses before arrival, the session is exited. If arrival, the trigger is actuated and a timestamp is transmitted to the microprocessor. Arrival of the subject is graphically represented on the screen, and a prompt is displayed for the subject to stabilize on the platform. The stability test is initiated and the trigger is set for the stability tolerance value, a value indicative of non-stability. The amplifiers are reset and the MOSFETs are disabled. The state counter is then incremented to State -1, the Stability Detect State 1.

Figure 21:
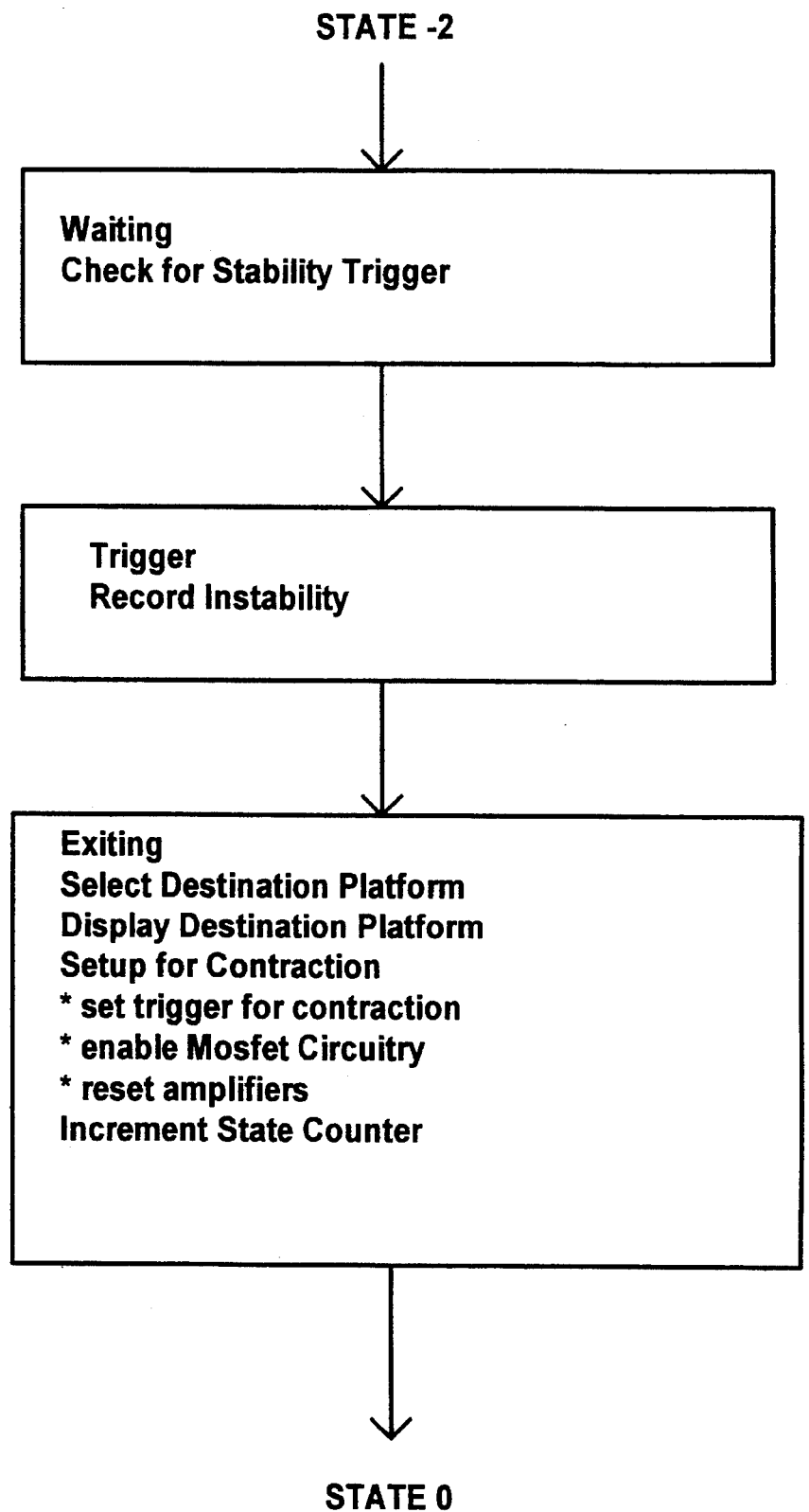

In State -1, as shown in FIG. 21, the the trigger awaits the stability tolerance. A trigger represents a predetermined number of samples exceeding the threshold value. At each trigger, the hardware interval timer provides a timestamp and the stability interval timer is reset. When no trigger occurs within the stability interval, indicative of stability, the current platform is identified and the hardware interval timer reset. A destination platform is identified and graphically displayed as a visual cue. When the visual cue is displayed and the hardware interval timer reset, the system is setup to wait for reaction movement from the current platform, the trigger is set for the contraction value, and the amplifier is reset for the landing platform. The state counter is incremented to State 0, the Contraction State.

Figure 22:
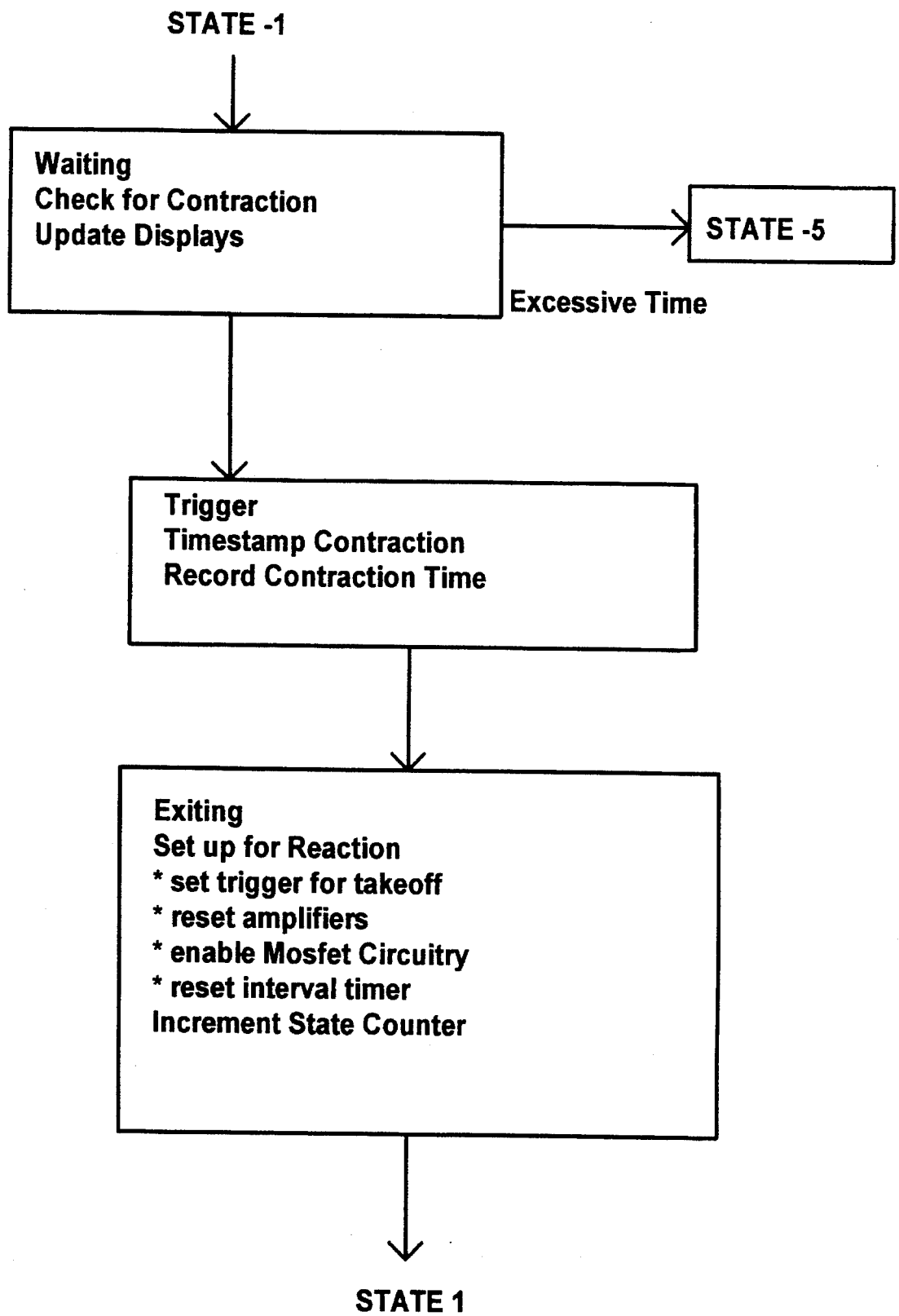

At state 0, as shown in FIG. 22, the hardware is monitoring for initial muscular force contraction. If the interval timer exceeds a predetermined amount, the system goes to the rest period fault state -5. At contraction, the contraction trigger is timestamped. The reaction time, i.e. the time interval between the contraction timestamp and the cue (when the hardware timer was reset), is determined and recorded. The trigger is reset for the takeoff value. The state counter is incremented to the State 1, the Takeoff State.

Figure 23:
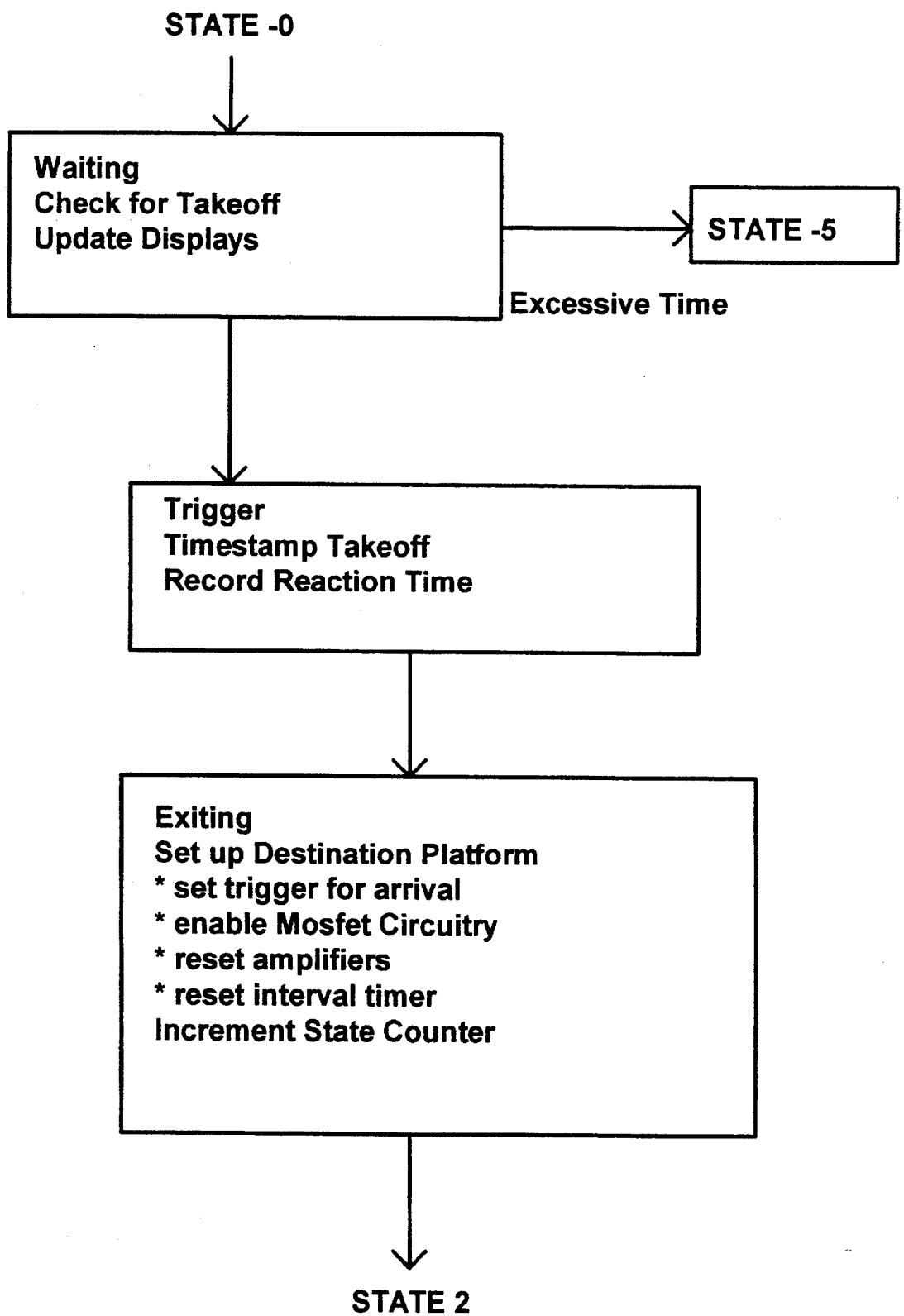

At State 1, as shown in FIG. 23, the hardware is monitoring for takeoff. If the interval time exceeds a predetermined amount, the system goes to the rest period fault state -5. At takeoff, the takeoff trigger is timestamped. The hardware interval timer is reset. The contraction time, i.e. the time interval between the takeoff timestamp and the contraction timestamp, is determined and recorded. The trigger is reset for the transit value at the destination platform, the MOSFETs at the destination platform are enabled, and the amplifier for the destination platform is reset. The state counter is incremented to State 2, the First Contact State.

Figure 24:
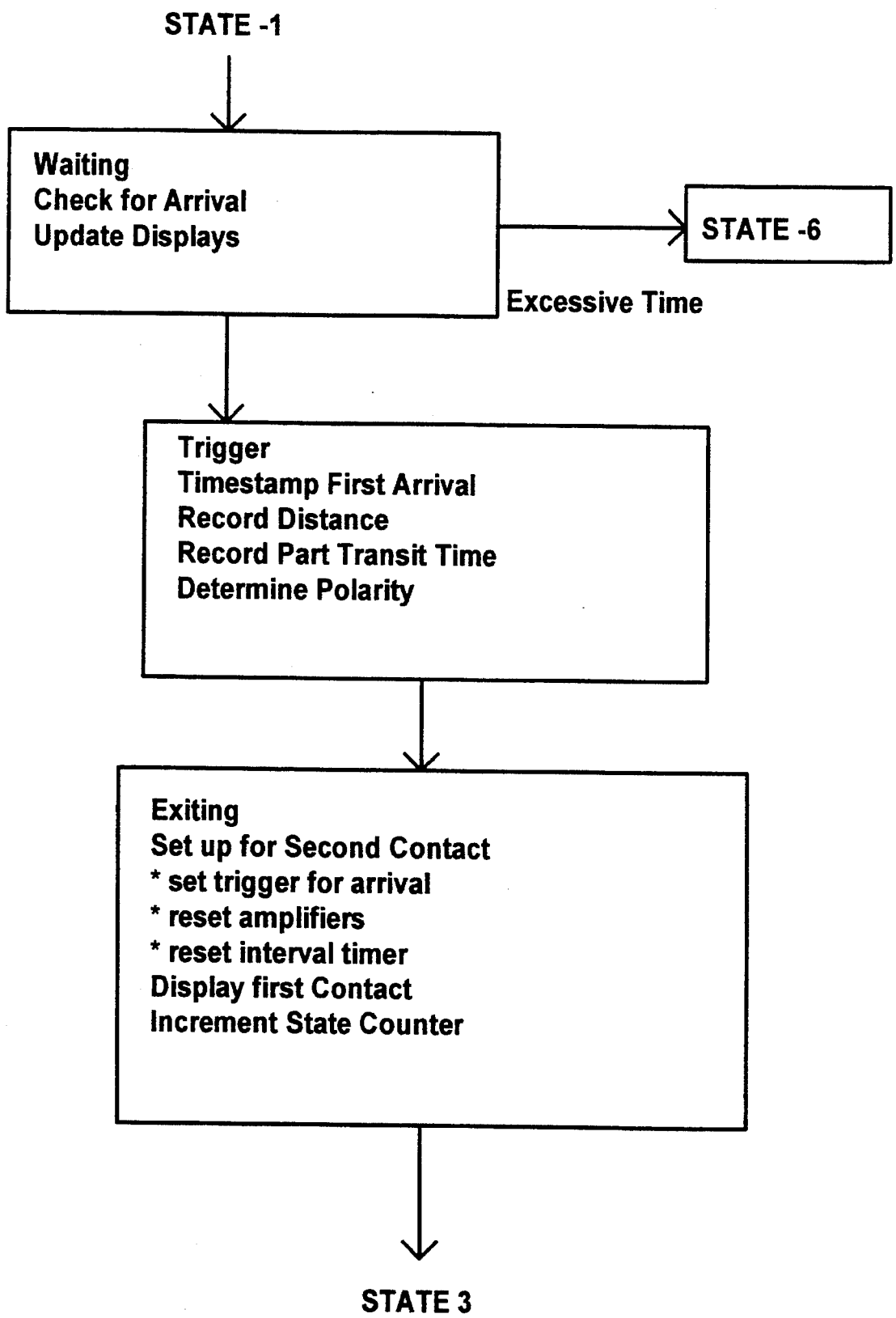

During State 2, as shown in FIG. 24, the system is waiting for the first foot contact at the destination platform, the clock displays are updated, and if the interval timer exceeds a predetermined time, the state counter is set to default state -6. At the trigger, the first component of transit time is timestamped and recorded and the known distance between the platforms is recorded. The trigger is reset for the transit value, the polarity of contact is determined, and thus the foot making contact first is determined. The hardware interval timer is reset and the first foot contact is displayed on the monitor. The state counter is incremented to State 3, the Second Contact State.

Figure 25:
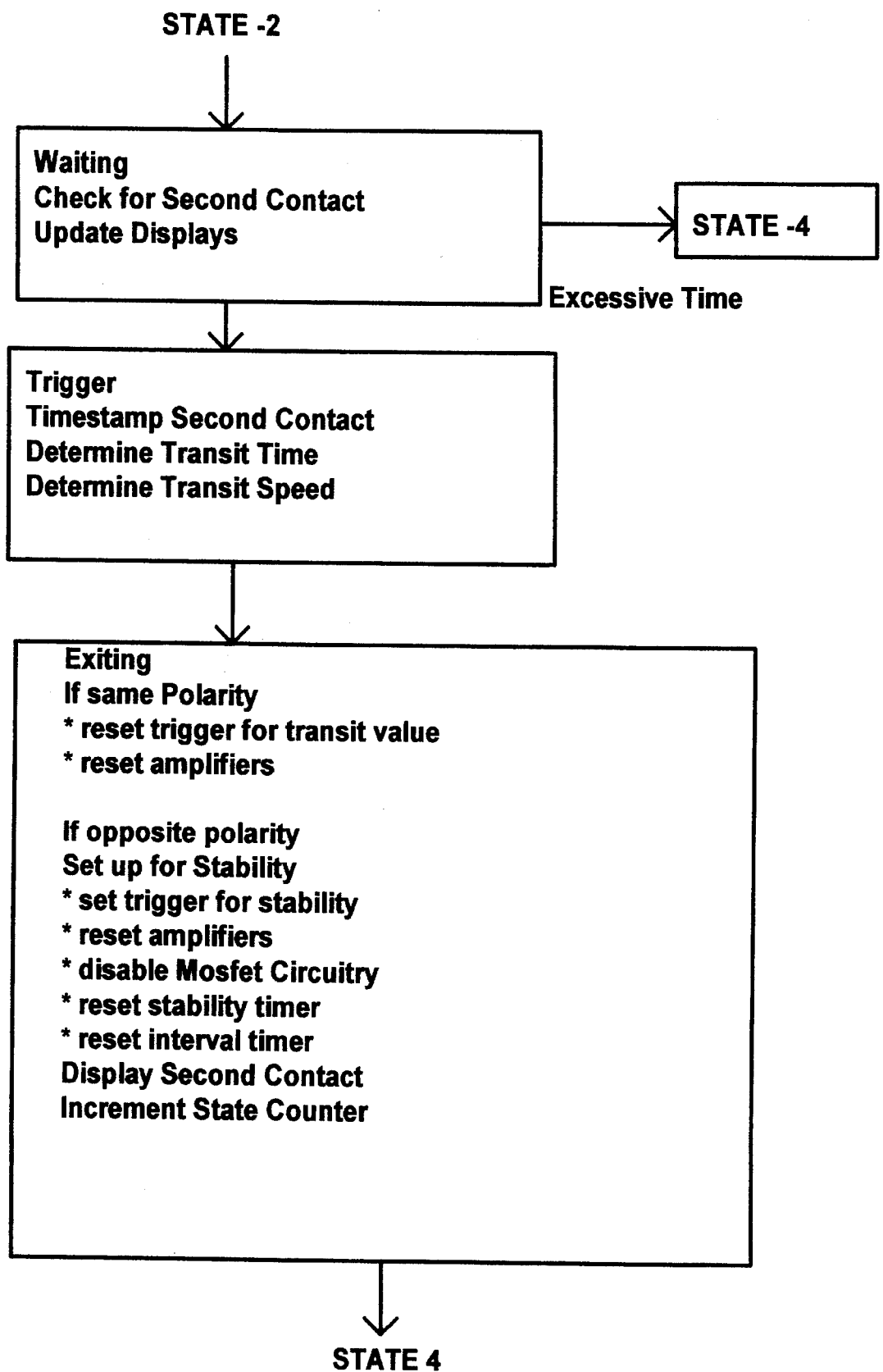

At State 3, as shown in FIG. 25, the system is awaiting contact by the second foot while the clock display is constantly updated. If the time interval exceed a predetermined time, the state counter is set to a fault state. At the trigger, the second timestamp is recorded. The transit time, i.e. the time interval represented by the sum of the difference between the second timestamp and the first timestamp plus the difference between the first contact timestamp and the contraction timestamp, is determined and recorded. If the polarity of the signal is the same as first foot contact, the trigger is set for the transit value again and the amplifier is reset for the destination platform and second foot contact is awaited once more. Otherwise, the stability test is readied, by setting the trigger for the stability tolerance value. The MOSFET's are disabled. The stability counter is reset. The interval timer is reset. The second pad is displayed as contacted, and the state counter is incremented to State 4, called Stability State 2.

Figure 26:
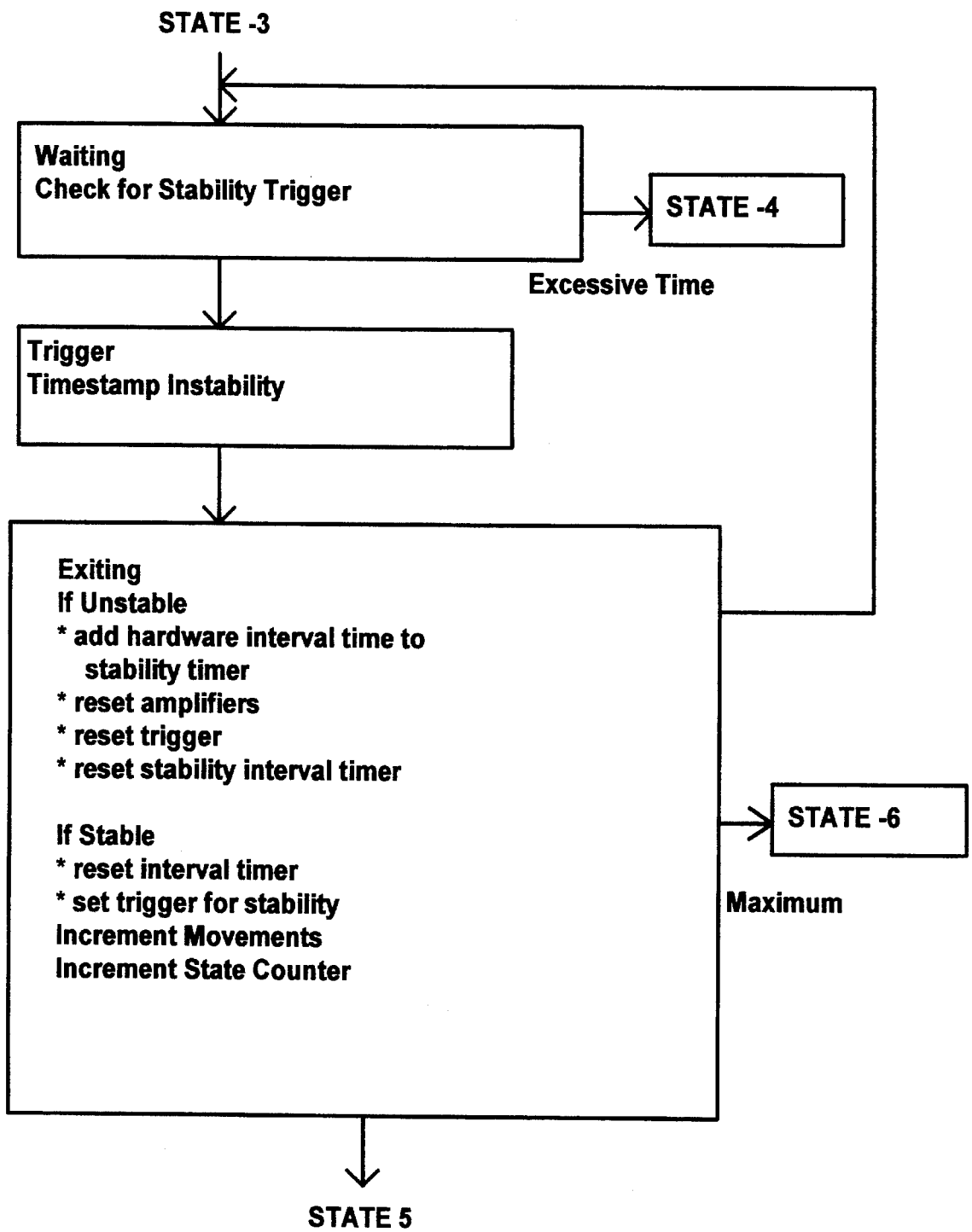

At state 4, as shown in FIG. 26, the system awaits the trigger for the stability interval, while the clock display is updated. If the interval timer exceeds a predetermined time without a trigger, the state counter advances to fault state -4. Each trigger timestamp within the stability interval is recorded and the platform amplifier, stability timer reset. When a trigger is not received within the stability interval, the stability time, i.e. the the time between the second foot contact and the last stability timestamp plus the the stability interval, is determined and recorded. If stable, indicating the voltage has not exceeded a predetermined amplitude for a predetermined time interval,the destination platform is designated as the current platform, the hardware interval timer is reset, the number of movements is incremented and, if equal to the maximum, the clock is stopped and the counter is advanced to Session Over State or State 6. The amplifier to the new destination platform is reset, the trigger is set for reaction value, and the stability timer is reset. The state counter is incremented to State 5, the Next Platform State.

Figure 27:
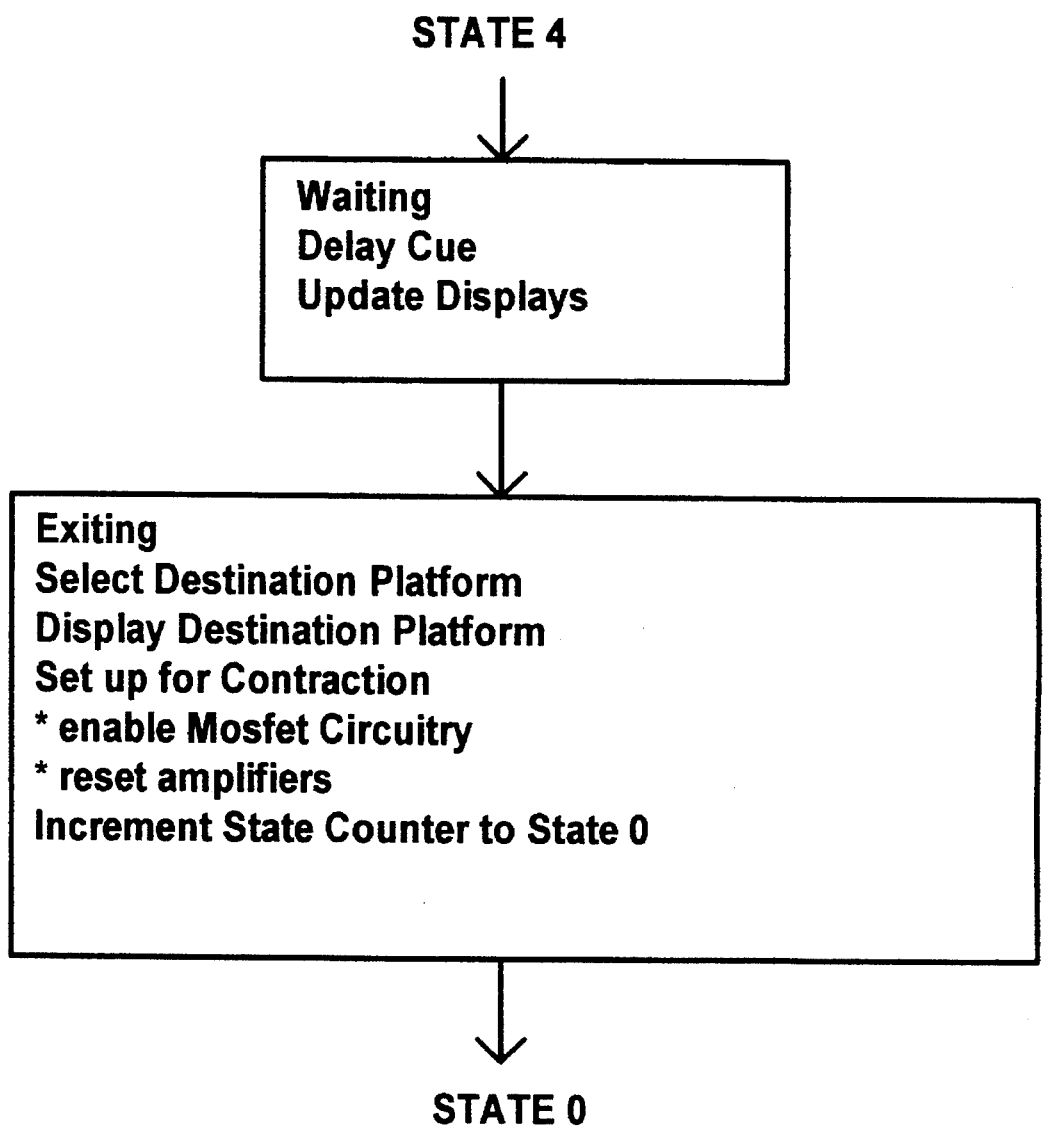

At State 5, as shown in FIG. 27, while waiting a predetermined delay is scheduled and the clock display is updated. After the delay, the current destination platform is designated as the initial platform. A new destination platform is displayed on the monitor, the trigger is set for the takeoff value and the amplifiers are reset. The state counter is set to State 0, the Contraction State and the test session continues.

Figure 28:
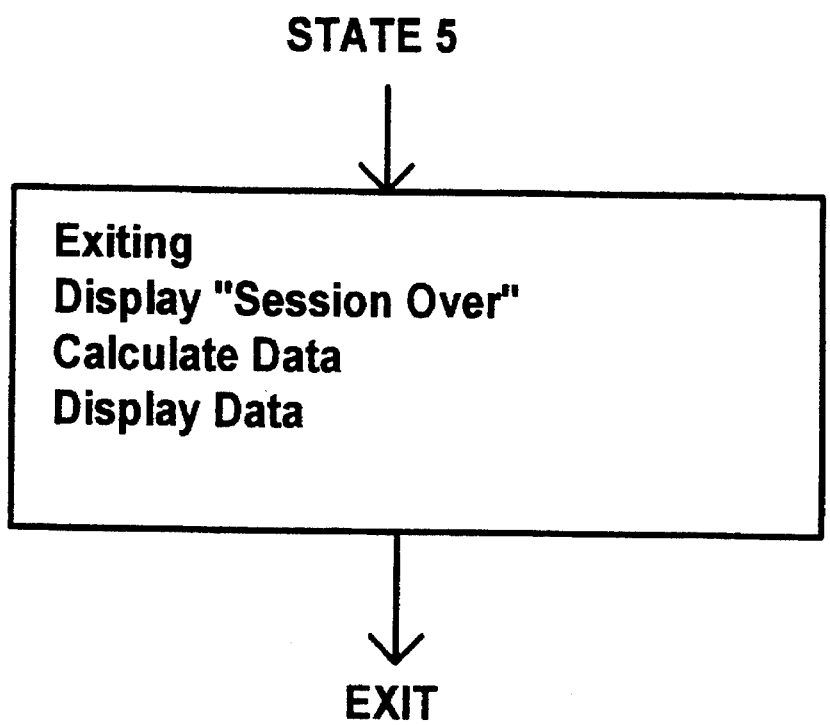

At State 6, as shown in FIG. 28, a "Session Over" message is displayed, the average data calculated and displayed in the aforementioned format shown in FIG. 11.

Figure 29:
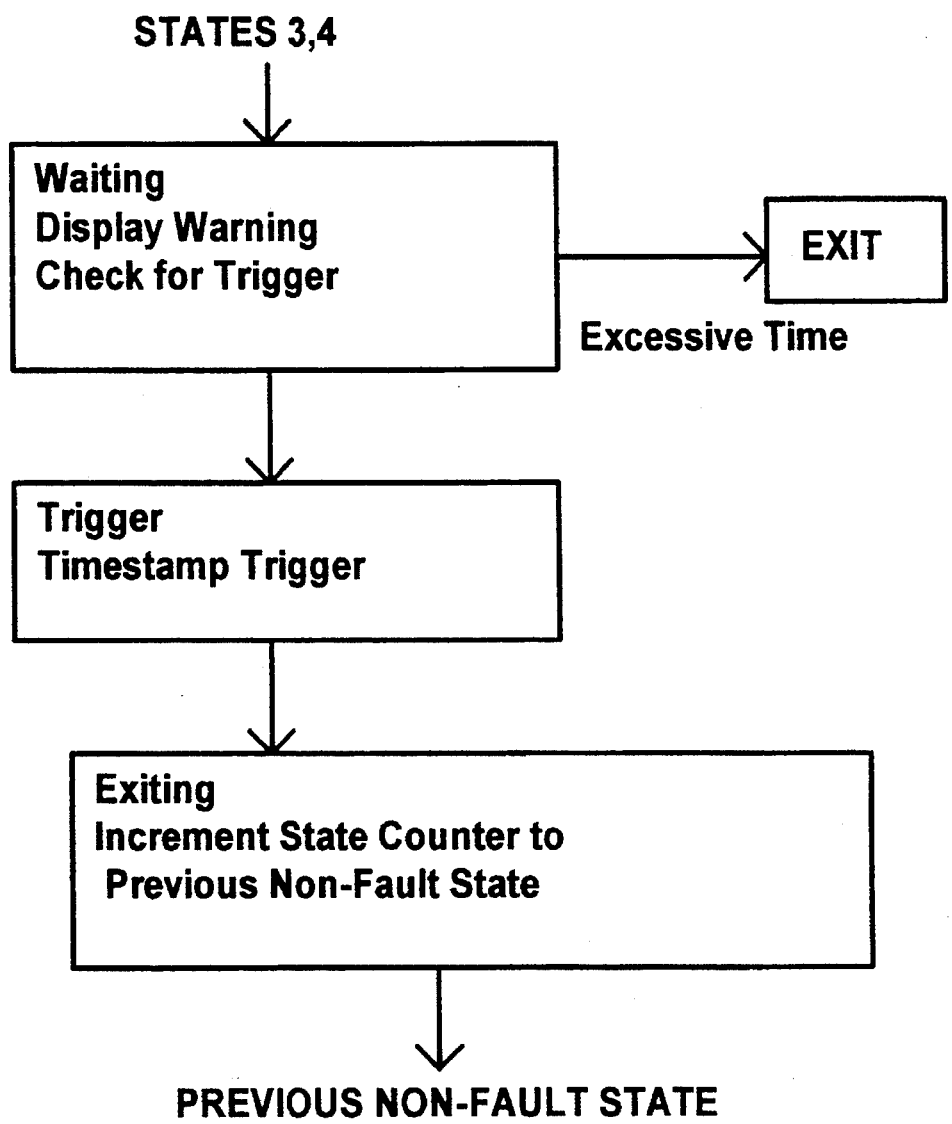

During the Prompt State, as shown in FIG. 29, the default states for the Stability State 1 and Second Contact State, a graphic prompt is displayed on the monitor and the system checks for stability or second contact. If the interval timer exceeds a predetermined time interval the session is exited. If a trigger occurs, the system is returned to the previous state and the trigger and exit functions are accordingly processed.

Figure 30:
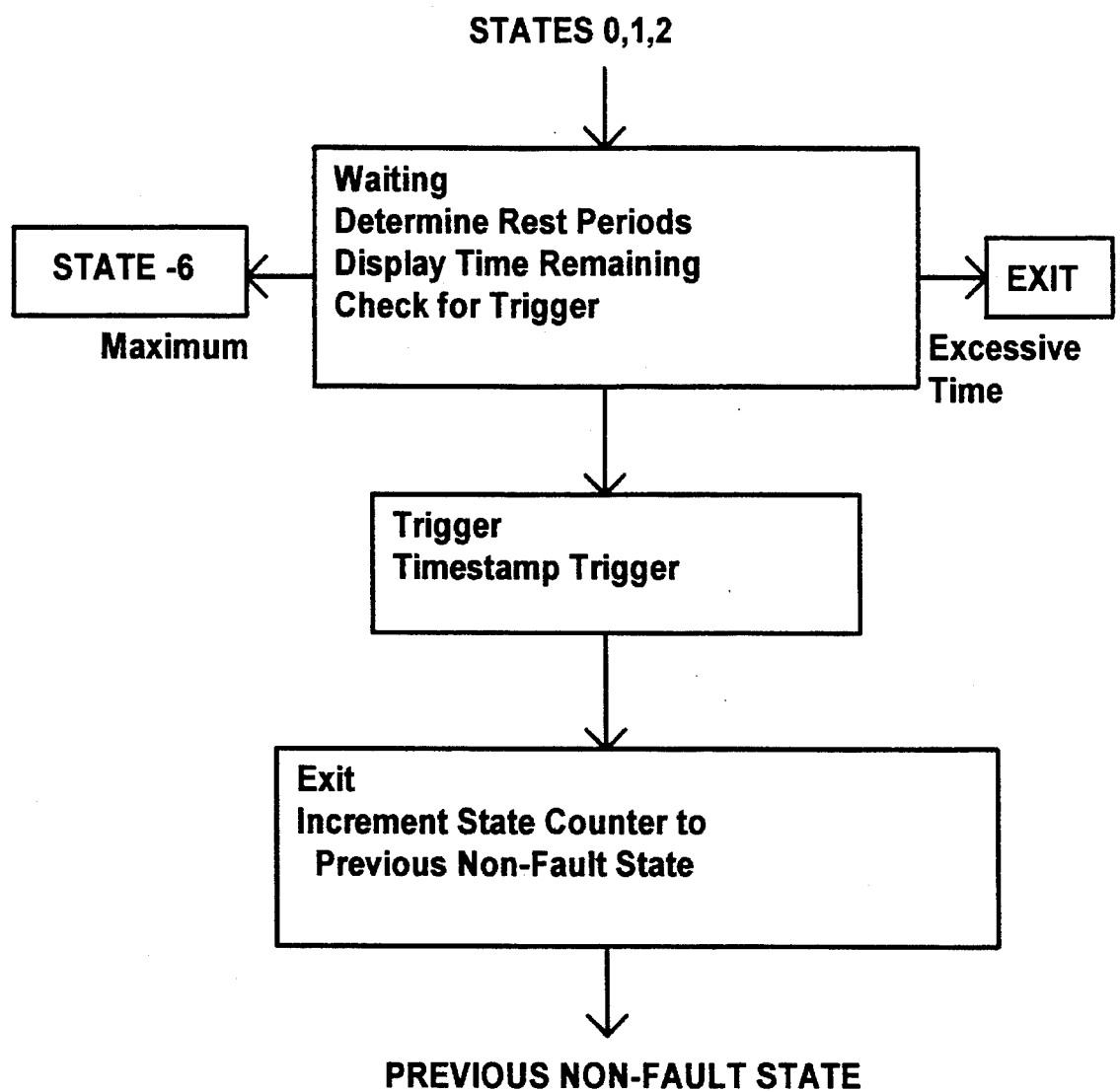

While in the Rest State as shown in FIG. 30, the default states for the First Platform State, and the Contraction State and the Takeoff State, the system determines the initial number of rest periods to that point. If a predetermined number have occurred the system is incremented to the No Arrival State, state -6. Otherwise the subject receives a visual prompt as to the time remaining in the rest period, and waits for stability or second contact. If the interval timer then exceeds a predetermined time, the session is aborted. If a trigger occurs, the trigger and exit functions of the previous state are processed.

Figure 31:
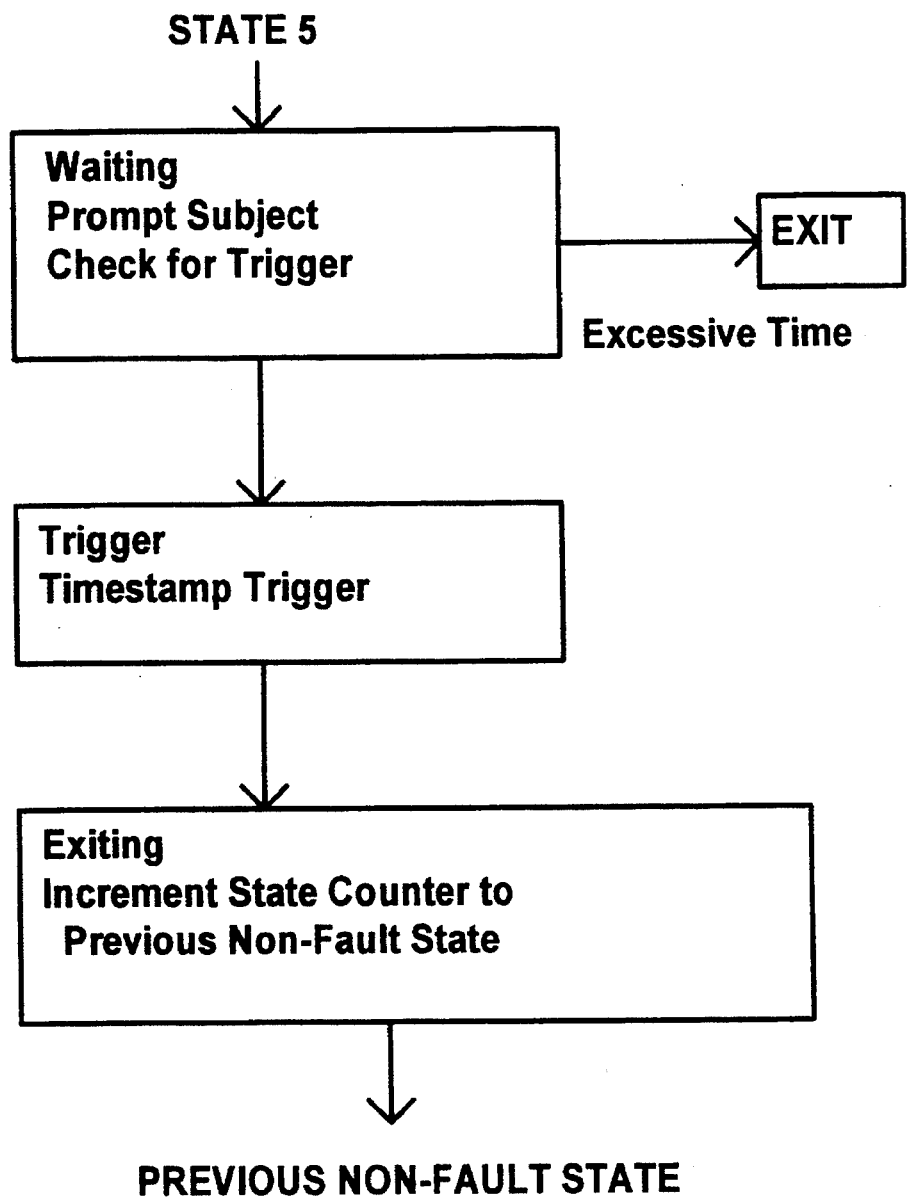

While in the No Arrival State, as shown in FIG. 31, the system checks for arrival at the target. If the interval timer exceeds a predetermined time, the session is aborted. If there is a trigger, the system returns to the previous non-fault state and processes the trigger and exit functions according to that state.

At the end of the test session, the components of the reaction movement sequence are displayed, in whole or in part as shown in FIG. 11. Therein, a comparison of performance for movement vectors to the right versus movement vectors to the left is provided. This comparison provides data which can detect, isolate, and quantify specific effects of musculoskeletal or neurological injury or pathology. Based on initial and follow-up test data, appropriate rehabilitation programs can be developed, progressed and monitored for effectiveness.

To ascertain an individual's maximum capability and to help insure maximum motivation in training applications, the aforementioned requirements must be combined with interactive control functions so that the system responds to the ability of the individual being tested. There are two general methods of interactive control, each of which has specific values for particular testing and/or training applications.

A "self-paced" or "real time" method can be used to trigger each subsequent movement cue at the instant of full contact at the intercept position specified by the previous cue, or a predetermined time interval thereafter. This allows the subject to control the pace of the activity from submaximal to absolute maximum performance through self control of the movement pace. Another use of this method is to control the time allowed to intercept a target at a specified position by basing the interval start time on the instant of change in loading initiating the takeoff movement.

The other method of interactive control of the visual cues bases incremental increases in functional demand or difficulty on the performance level of an immediately preceding series of movements. The functional demand is progressively increased until the subject's maximum performance level is attained and measured. This method provides more realistic simulation of competitive play because it allows a certain number of target misses or failed interceptions.

In addition to the large number of possible movements, the visual specificity of the visual cues on the monitor and the varying focal range over which the cues appear requires the subject to make true reaction movements. The reaction movements include perception and interpretation of the cue, and decisions on movement pattern and direction. This requires realistic visual, neurophysiological and biomechanical reactions, as opposed to preplanned movements executed in response to non-specific starting cues appearing predictably in a focused location.

The testing or training session can be any appropriate duration, but generally consists of the following series of interdependent events:

1. A visual movement cue is displayed on the video screen that is non-predictable in its timing and/or the functional response it specifies.

2. The player responds to the visual cue by executing the reaction movement sequence to move from the current weight-bearing pad position to a weight bearing position at the designated target or intercept position.

3. The system responds to the player's actions by precisely measuring each component of the reaction movement sequence and triggering a subsequent movement visual cue that may be based on one or more components of the subject's performance.

This series of interactive player and system responses is repeated until a specific number and combination of movements or time has been completed or until an incrementally progressed level of difficulty exceeds the player's capabilities.

It is of particular significance that the system can apply the previously described methods of interaction with the subject based on one or more specific components of the reaction movement sequence. Virtually instantaneous system responses to the subject's reaction movement, intercept position, contact, and/or stabilization can be used to design programs that emphasize a particular aspect or component of performance. This same capability can be used to control the challenge presented, therefore, controlling the cardiovascular and musculoskeletal demands placed on the subject.

Similarly, this capability can be used to design sport specific simulations that require the athlete to perform actual game movements that simulate athletic activity. This allows both training and testing of an athlete's performance in a particular scenario or under special circumstances. For example, a program can emphasize certain sport-specific responses at sufficient intensity and for long enough duration to measure the effects of fatigue on an athlete's visual perception, reaction time, movement speed, balance and stability.

Other applications of comparisons among component measurements and/or right versus left movement performance include: assessment of the effects of various training programs on each component of the reaction movement sequence and overall reaction movement speed; optimal player positioning to take advantage of a measured difference in overall reaction movement speed to the left or right.

By having the session fulfill all the requirements for optimal training of reaction movement skills through the large number of possible movements, the visual specificity of movement cues and the focal range over which these cues can appear insure a lack of predictability that requires the subject to make true reaction movements. These reaction movements include perception and interpretation of the cue, the decisions on movement pattern and direction. Incorporation of these factors results in completely different and more realistic visual, neurophysiological and biomechanical challenges than previously available technologies that rely on pre-planned movements executed in response to non-specific starting cues which appear predictably in a focused location. Therein, no head tracking is required, inasmuch as the eye does not have to scan the horizon searching for cues.

Additionally, reaction time can be an important parameter to consider when evaluating an athlete's recovery from any injury. For example, though an athlete may have recovered physically from an injury, he may not have regained the confidence to explode off the injured limb; his hesitation would be reflected in longer reaction times.

Figure 32:
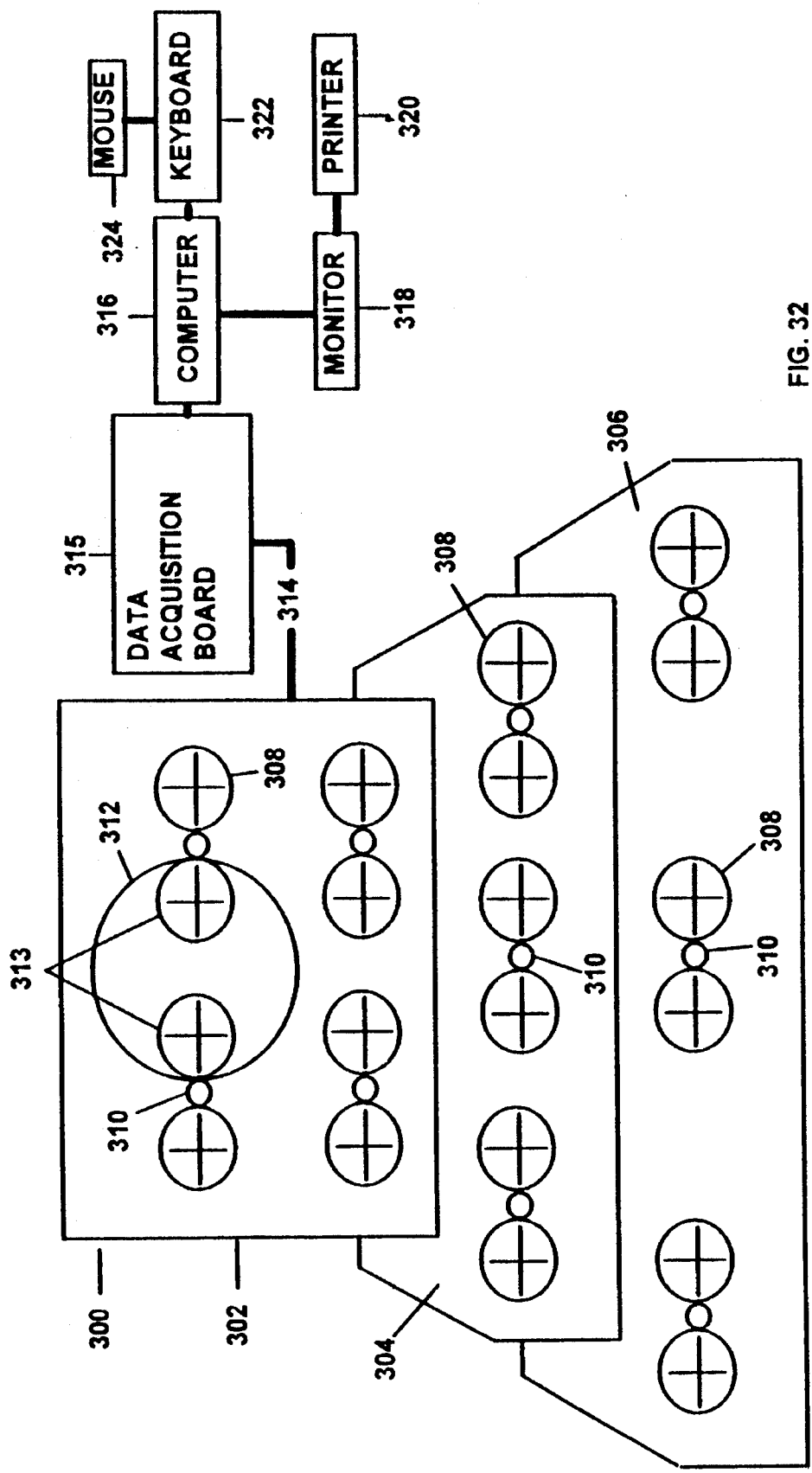
FIG. 32 is a plan schematic view of an embodiment of the testing and training system shown in FIG. 1.

Specialized protocols for progressive closed kinetic chain rehabilitation using specific activities, movement sequences and real-time data feedback to guide patient effort and control/limit musculoskeletal stress may be utilized in the above described embodiment and the embodiment shown in FIG. 32.

Therein, in addition to interactive display control functions, system computers monitor and record performance parameters so that isolated limb function comparisons are readily available using the system's test record and database. These applications do not require any constraints, attachments or set-up time—major factors in clinical efficiency and patient compliance.

Testing and rehabilitation protocols can be implemented as soon as the patient is ready for weight-bearing activity. Static activities like stance stability protocols are suitable for early intervention and can even be performed while assistive devices are being used. For the later stages of sports rehabilitation, activities can be designed to challenge the limits of any athlete.

The primary rehabilitation applications utilize simple, direct measurement and feedback of actual functional performance, and the capability to impose controlled weight-bearing movement demands. Throughout the rehabilitation program, functional deficits can be quantified and movement demands can be controlled and progressed to limit musculoskeletal stresses as appropriate for the patient's current status and rehabilitation goals.

Referring to FIG. 32, there is shown a testing, training and rehabilitation system 300. The system is particularly well suited for making bilateral comparisons of the aforementioned performance parameters, i.e. reaction time, eccentric ground force time, concentric ground force time, total ground force time, transit time and speed, and stability time in accordance with recognitive and accepted testing and rehabilitation protocols. In many of such protocols, the analog signal of interest is generated from only one pad.

Figure 35:
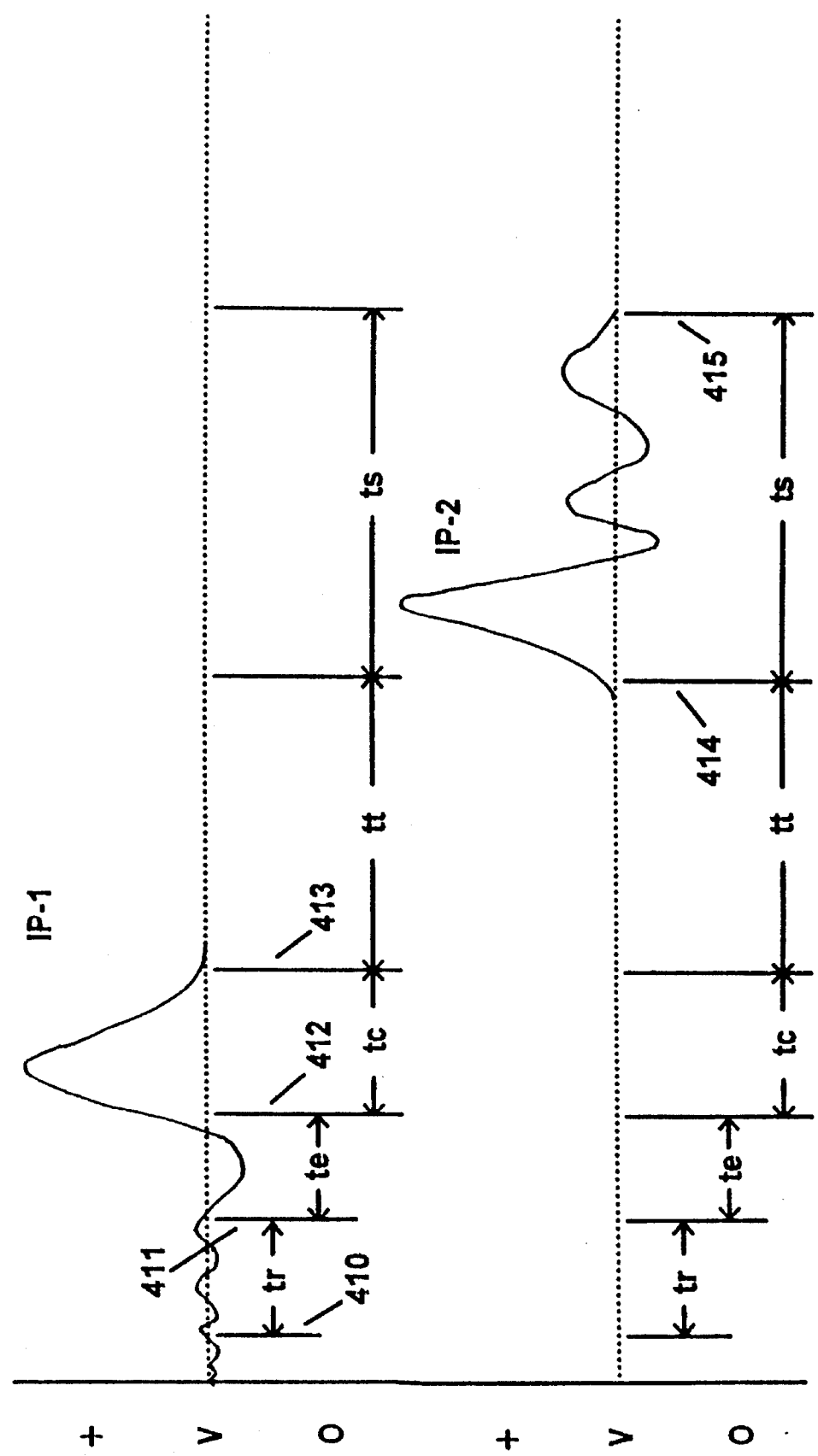
FIG. 35 is a representative waveform for the analog signal from two non-paired platforms.
Figure 37:
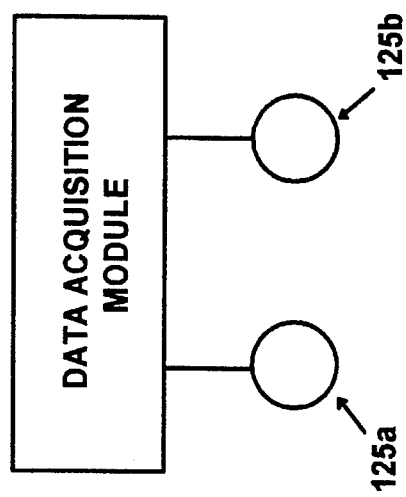
FIG. 37 is a schematic diagram of the connection between two non-paired platforms.

Referring to FIG. 35, there is shown a representative waveform for analog signals transmitted from two non-paired platforms, $125_a$ and $125_b$, FIG. 37, to the data acquisition module for a subject at rest at a first intercept position, IP-1. Thereat, only one limb of the subject is in contact with a pad. Each pad is a member of two distinct groups of paired pads. The other member of each group is located at a distance from the takeoff position to insure it does not interfere with the measurement or corrupt the signal being measured.

The subject receives a visual cue directing movement to a second intercept position, IP-2, and executes a a single limb movement sequence to that intercept position IP-2. During an initial time interval, the subject has a stable stance represented by low level, low frequency fluctuations. The visual cue is initiated at timing point 410. At timing point 411, the limb initiates reaction movement starting with an eccentric phase, or unloading of the body weight, typically producing a negative slope waveform. The time interval between timing points 410 and 411, $t_r$, represents the aforementioned reaction time. At timing point 412, the eccentric phase ends, and the concentric phase begins and loading of body weight occurs by pushing away from the platform, typically producing a larger magnitude positive slope waveform. The time interval between timing points 411 and 412, $t_e$, represents the eccentric ground force time. At timing point 413, the concentric phase ends and the subject has vacated the first platform for movement to the next platform or intercept position. The time interval between timing points 412 and 413, $t_c$, represents the concentric ground force time. The time interval between timing points 411 and 413, the sum of $t_e$ and $t_c$, represents the total ground force time.

Timing point 414 signals the beginning of the landing phase at the second platform. The time interval between timing points 413 and 414, $t_t$, represents the transit time. This platform experiences a large sudden onset of the subject's body weight that drives the waveform to some positive voltage offset. Dynamic filtering of the MOSFETs may be employed at this stage to filter lower frequency noise and prevent false triggering of the stability analysis. Timing point 415 represents the completion of the stability phase wherein the voltage amplitude has not exceeded a predetermined value for a predetermined time. The time interval between timing points 414 and 415, $t_s$, represents the stability time.

More particularly, the system 300 includes a field 301 comprising a front field 302, a middle field 304 and a rear field 306. The front field 302 may be operated as a single system. The front field 302 and the middle field 304 may be coupled and operated as a single system. The three fields may also be coupled and operated as a single field.

Circular impact platforms 308 are incorporated in each field. The platforms 308 are arrayed in pairs defining intercept positions 310. A single platform 312, larger in diameter than the platforms 308, is located in the center of the front row of the front field 302. The platform 312 has a single perimeter sensor as described above. The platform 312 includes two target positions 313 depicted thereon, which are not necessarily independently sensed. The positions 313 are paired with an adjacent platform 308 to define an intercept position. Thus a subject standing at the intercept position with a limb on each platform will have the body's center of gravity positioned substantially midway therebetween.

The output leads 314 of the sensors on the platforms are coupled to a data acquisition module 315 which is coupled to a computer 316, a display monitor 318 and a printer 320. The computer 316 is connected to an input keyboard 322 for inputting relevant data and controlling the test protocol.

The system 300 is particularly well adapted for bilateral comparison of the aforementioned parameter, i.e. reaction time, ground force time, transit time and speed, and stability time in accordance with recognized and accepted testing and rehabilitation protocols.

Figure 33:
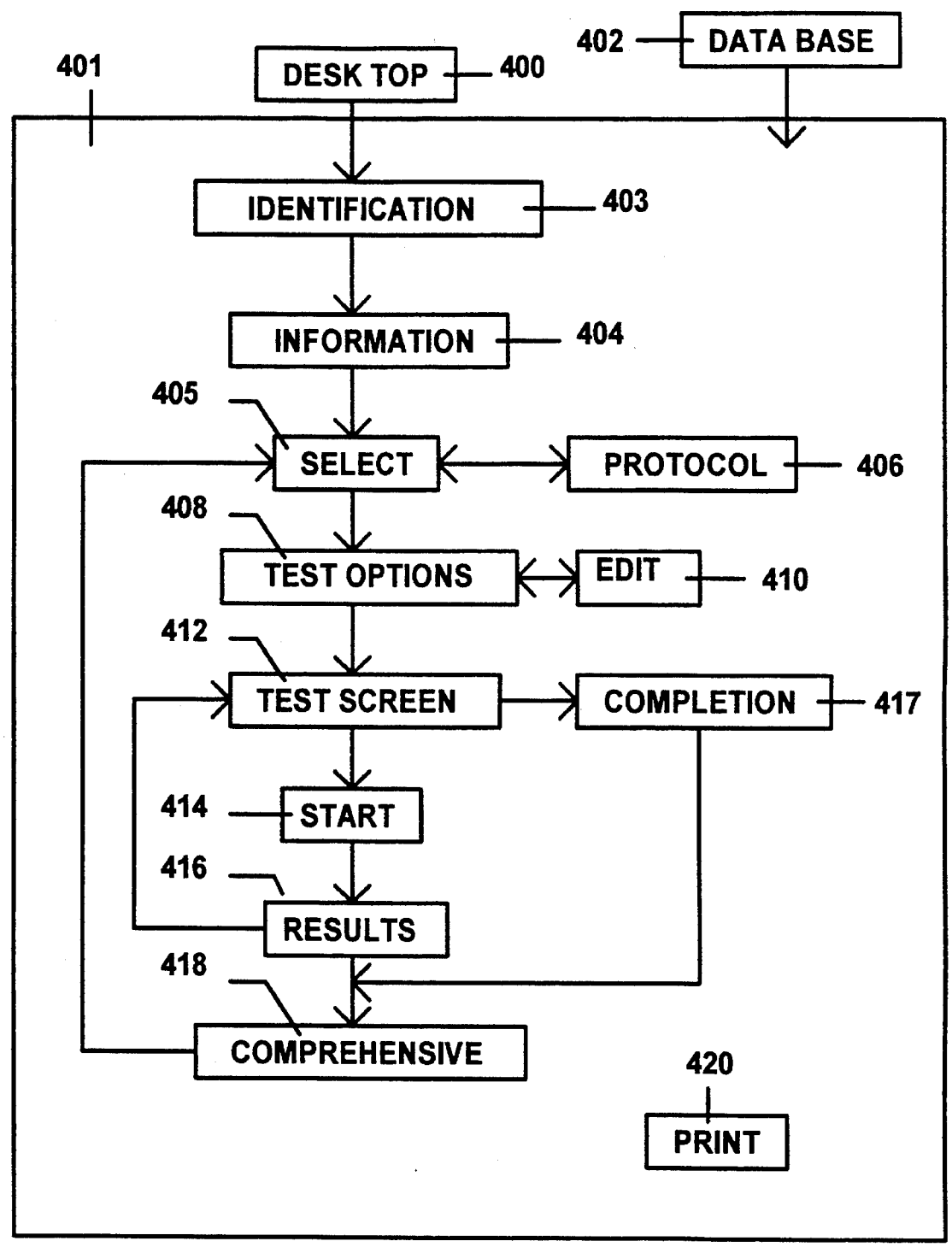
FIG. 33 is flow chart for the operation of the system shown in FIG. 32 during a training protocol.

A flow chart for a testing protocol, a linear reaction/stabilization hop test, is shown in FIG. 33. More particularly, in this test protocol, the subject will start on a platform at one side of the back row of the front field standing on one designated leg and facing forwardly toward the platforms aligned thereon. At an audio or visual cue, the subject will hop on the one leg to the next pad and stabilize leg and body movement until the magnitude of the signal from the sensor does not exceed a predetermined voltage threshold for a predetermined time interval. Upon stabilization, the subject will be given a biofeedback cue and released for movement to the platform at the next position. The test may be repeated on the same leg or performed on the other leg. At the end of each leg set, a report is issued as described below. Leg sets are performed continuously and the test terminated at the user/evaluator's or subjects discretion. Preferably, the computer is an IBM compatible DOS-based computer and operates with a Microsoft Windows type graphical interface.

Upon startup a desk top 400 is displayed and presents the user various icon options such as the test system, and other installed programs. If the test system program 401 is selected, a subject identification screen 403 is displayed requiring the entry of a subject identification number or code. This selection can be cancelled, if desired, and the existing subject can be retrieved by searching the database. All protocols and acquired data in the test program are coupled to a data base 402.

Upon entry of the required data, a subject information screen 404 is displayed and the user is prompted to enter subject identification, such as name, identification number, referring physician, involved side of the injury and type of injury. If the person has been previously evaluated, entry of name or identification displays current information on the evaluations for the subject. Pull down screens are displayed on the subject information screen, including an activity menu, a subject menu allowing entry and revision of subject information, a reports menu for prior information on the subject, data base for accessing subject information based on desired entry categories, utilities for system configuration, and help and exit selections.

After data entry, a select activity menu 405 may be selected, outlining options for the primary testing and rehabilitation protocols. From the activity menu 405, the various protocols for the selection are displayed. Also displayed are the types of movement to be evaluated, such as forward, backward, medial or lateral, in this instance forward movement of the subject. After selecting, the user may select describe protocol 406, which outlines background information on the selection. If satisfactory, the user returns to the select activity menu 405, and continues the session or returns to the subject information menu.

By selecting the continue option, a test options screen 408 is displayed. The screen automatically defaults to the uninvolved, non-dominant leg, but may be changed by selecting the other options. If the selected test requires stability measurement, an appropriate indication is displayed and the user may select an edit function which will display a stability adjust screen 410. This permits selection of certain default setting (high, low or medium) and displays the duration and magnitude parameters associated therewith. The user may also select a custom setting through data entry to apply for the current evaluation. If satisfactory, the user selects a proceed option and is returned to the test options screen. If it is desired to terminate the session at this point, the user may select a cancel option and is returned to test selection screen. On the test options screen the user may optionally select additional criteria bearing on the test, such as footware, motion restrictions for the test, vision limitations, and barrier information. If satisfactory, the user may select a continue option, and a test screen 412 is displayed.

The test screen 412 displays a visual replication of the field and platforms involved in the test as in the first described embodiment. The screen also displays starting instruction for the subject including initial position, starting leg and body orientation for the test. The current information regarding sets or repetitions completed to date, leg by leg, is also displayed. Upon selection of the start option 414, in accordance with the selected protocol, the series of platforms are sequentially highlighted. At each platform, the subject must obtain the selected stability index, at which time an audio and/or visual cue is provided indicating compliance and releasing the subject for movement to the next designated position.

Upon completion of the last movement involved, the results of the set are displayed on a results screen 416. The results screen 416 displays the overall results for the test on the selected parameters, and the individual measurements for each movement event. Based on the displayed results, the user may accept the set, whereat the data is entered in the subjects data file, or redo the set. Either select returns to the test screen. Upon return, the test may be repeated for the same leg or a test other leg may be selected. For the latter, revised screen instructions are displayed in accordance with the protocol. The movement sequence is again initiated by start option 418 and proceeds as outlined above. When the user determines that the desired sets involving a desired comparison between the legs has been completed, a completion option 417 may be selected, which displays a comprehensive status report screen 414 on the tested protocol. This displays the subject information of the patient on the screen, describes the test protocol and parameters, and best and average information related to the tested parameters, based on single or overall information as well as displaying and identifying information on deficiencies. Thereafter, the user may select print 420 for providing a printed report of the test, or save the data in the data base and return to the select test screen 404. Individual movements may be optionally printed.

Figure 34:
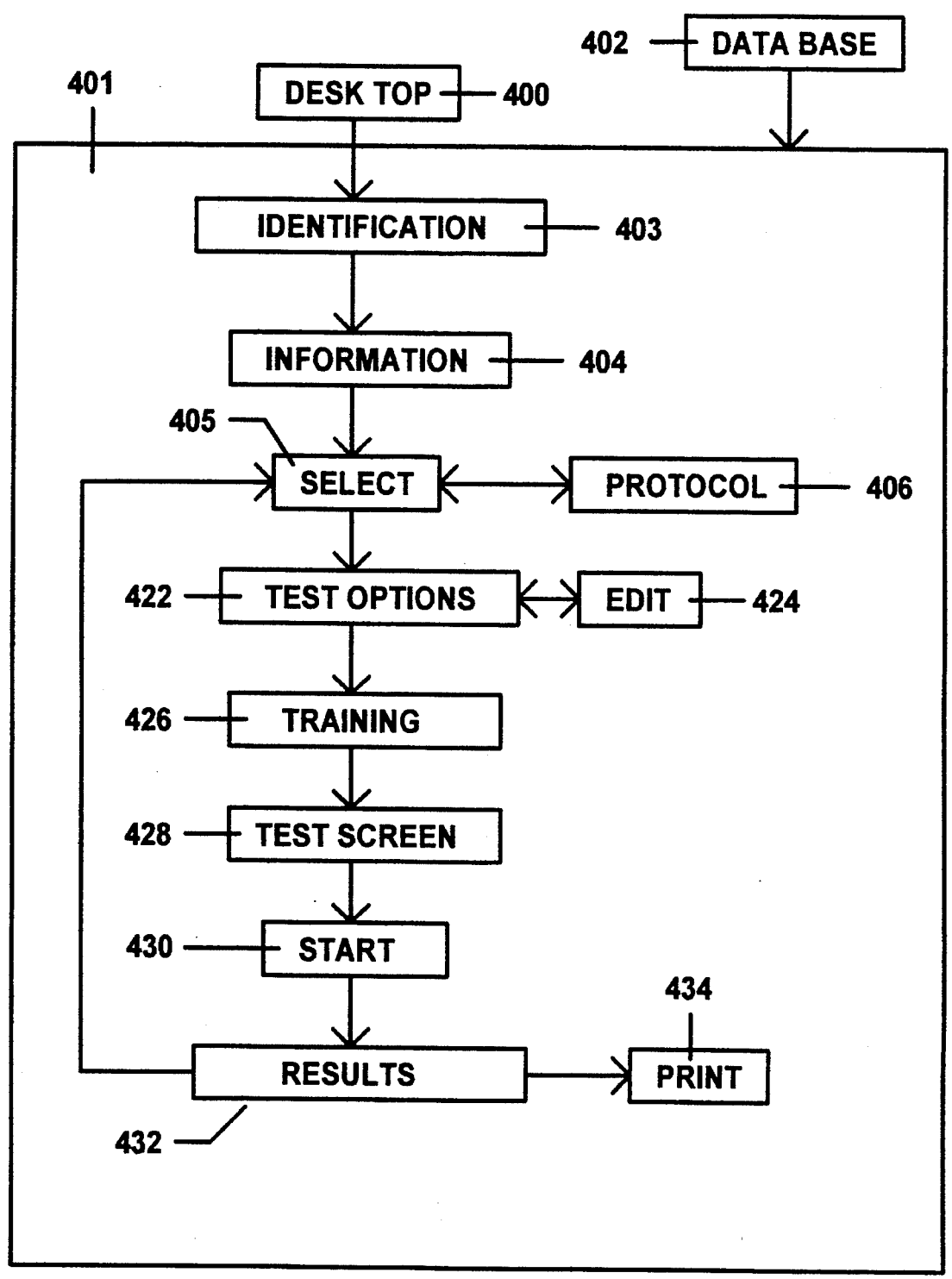
FIG. 34 is flow chart for the operation of the system shown in FIG. 32 during a rehabilitation protocol.

A test program for a rehabilitation protocol is shown in the flow chart of FIG. 34. At start up the desk top 400 is displayed as described above. The test program 401 is coupled to the data base 402. If the test program 401 is selected, the subject information screen 403 is displayed requiring entry of identification and the subject information screen is thereafter displayed. The user then selects from the activity menu 404 the desired rehabilitation protocol, by way of example a linear reaction/stabilization hop test. In this test, the subject starts at one end of the second test row and hops on the selected limb to the next platform, stabilizes, and when stabilized is given a biofeedback cue, audibly or visually, and is thereby released for movement to the next platform and similarly measured until the last platform. The test is repeated for a selected number of sets with a rest period therebetween. The measured parameter is contraction or ground force time. The objective of the test is to complete the test within minimum and maximum ground force times which challenge the subject, but which are not too easy or too difficult for the present physical status.

More particularly, after the select activity screen 405, a test options screen 422 is displayed, requiring the user to select the test leg, and accept or edit through a edit stability screen 424, similar to screen 410. After entry, the user is returned to the test options screen 422, and if continued a training options screen 426 is displayed. This screen allows entry of the number of sets for the selected protocol, the rest period therebetween, and the minimum and maximum values for the target parameter, in this instance ground force time.

If acceptable a begin test option is selected and the test screen 428 is presented, depicting the test field the initial platform and the designated second platform. After selecting the start 430, a countdown period is provided for the subject to reach the initial platform. The countdown period is displayed on the screen and expiration is audibly and visually cued. The subject then traverses the platform sequence, trying to attain ground force times within the selected range, stabilizes on the platform and is released to the next platform. After each hop the ground force time is visually displayed and the subject is informed whether the target range for ground force time has been achieved. At the end of the leg set, a countdown period is displayed on the screen signalling the start of the next set for the exercise. This is repeated until all sets have been completed.

Upon completion of the selected sets, a report screen 432 is displayed, listing subject information, the protocol selections, the percentage of movements within the target range, the average parameter value and the standard deviation thereon. The results may be printed, edited and thereafter exited to the subject information screen 404 for a repeat of the same or another protocol, or exit from the session.

The rehabilitation protocols can thus test and document progress of the subject until maximum medical improvement or other specific rehabilitation criteria are achieved.

These measurements quantify the net functional effects and deficits resulting from injury or dysfunction, and provide significant advantages over more isolated measurements. Movements and stability deficits of the involved to uninvolved limb are precisely identified. Progress resulting from the rehabilitation program or training regimen is easily monitored and comparisons of performance among individuals or to normative data are available.

All protocols use direction and distance of movement (vector/distance categories) as a basis for comparison of performance. Comparing specific component measurements for movement vectors to the right versus movement vectors to the left often identifies functional deficits that are not detected by other types of testing. When deficits are identified, these same vector/distance categories can be used to apply controlled, progressive training demands during rehabilitation. Functional demand is increased within patient tolerance, and treatment effectiveness can be monitored on a visit to visit basis by tracking performance data.

It will be appreciated that for either of the systems described above, musculoskeletal stresses can be controlled or modulated by selecting specific movement sequences that use directions and distances appropriate for the patient's limitations. Foot pattern movement instructions can also be used to control stresses and/or to improve quality of movement. For example, the patient might be instructed to use multiple small "shuffle" steps, cross-steps, hops, walking or giant strides to transit a specific distance, or to backpedal or pivot and stride to certain vector/distances. For further control of progressive demand, immediate patient feedback of specific measurements can be used to limit efforts to targeted submaximal levels. For example, instructing the patient to consciously control Reaction and Ground Force Times within specified displayed levels will result in lower initial acceleration forces. A specialized real-time feedback display is provided for this application.

In addition to quantifying the time based parameters of the signal generated during accelerations and decelerations from the platform, the signal may also be analyzed with respect to amplitude and time to quantify force related measurements such as push off forces generated by each limb during the ground force time.

It will thus be appreciated that the above described embodiments provide a system for generating movement cues on a display device, in a non-predictable sequence, for directing the user's movement forwardly, backwardly and laterally between visually designated positions, and measuring changes in loading of each limb during such movement to provide quantifiable information with regard to fitness and performance.

This information may be gathered through other electrical and mechanical approaches. For instance, variable resistive inks which provide a signal indicative of foot pressure may be used as shoe insoles to provide the force change indicia and switch mats or the like may be employed to confirm arrivals and departures between positions. Rather than insoles, accelerometers may be used to generate the force related changes. Further, rather than switch mats, a multiplicity of small force sensing elements could be arrayed over the entire field and thus indicate the instantaneous position of each limb during the directed movements. Additionally, a grid may be incorporated in the field using piezo film elements or variable resistive inks for generating force and location information. The degree of spatial resolution would be a function of the density of the sensored locations and the process capabilities of the associated hardware.

The present system fulfills all the requirements for truly valid testing of reaction movements. This is important because unplanned movements involve significantly more complex neural pathways than pre-planned movements.

What is claimed:

1. A reaction movement sequence system for directing and assessing leg movement performance of a subject, comprising:

a. video means;

b. field means for confining subject leg movement including a plurality of intercept positions each of which comprises a pair of laterally spaced foot impact pads geometrically oriented to locate the subject frontally with respect to said video means when the subject is positioned thereon and arrayed on the field in predetermined positions to provide predetermined relationships with respect to the other pads and reachable by lateral, forward and backward movements of the subject;

c. analog sensor means operatively associated with said impact pads providing a signal in accordance with changes in loading on said impact pads;

d. first means operatively associated with said video means for presenting thereon a replication of said field means;

e. second means operatively associated with said first means for presenting a visual cue on said replication of said field means at a target intercept position corresponding to one of said plurality of intercept positions different from the current intercept position of the subject;

f. timing means for receiving said signal from said sensor means and determining (1) the time interval from said visual cue until commencement of movement by the subject for exiting said current intercept position, (2) the interval from said commencement of movement until the subject reaches said target intercept position, and (3) the time interval until said subject reaches predetermined stability on said target intercept position;

g. third means for initiating another visual cue when said subject reaches said target intercept position, said third means generating subsequent visual cues in a nonpredictable fashion as to timing and prescribing a course of subject movement between said current intercept position and subsequent intercept positions; and h. means associated with said timing means and said video means for graphically presenting on said video means information related to said timing intervals.

2. A reaction movement sequence apparatus for directing and assessing leg movement performance of a subject, comprising: a plurality of intercept positions, each intercept position comprising foot impact pads geometrically oriented and arrayed on said field means to provide predetermined relationships with respect to the other pads and reachable by lateral, forward and backward movements of the subject; display means for graphically representing said intercept positions; analog sensor means operatively associated with said impact pads providing a signal in accordance with movement on said impact pads; first means operatively associated with said display means for presenting a visual cue on said display at a target intercept position graphically corresponding to a destination intercept position different from the current intercept position of the subject; timing means for receiving said signal from said sensor means and determining (a) the time interval from said visual cue until commencement of movement by the subject for exiting said current interception position, and (b) the time interval from said commencement of movement until the subject reaches said destination intercept position; second means for initiating another visual cue when said subject reaches said destination intercept position, said second means generating subsequent visual cues in a nonpredictable fashion as to timing and prescribing a course of subject movement between said current intercept position and subsequent destination intercept positions.

3. A reaction movement sequence system for directing and assessing leg movement performance of a subject, comprising: a plurality of intercept positions each comprising foot impact pads geometrically oriented and arrayed on said field means to provide predetermined relationships with respect to the other pads reachable by lateral, forward and backward movements of the subject; display means for graphically representing said intercept positions; analog sensor means operatively associated with said impact pads providing a signal in accordance with movement on said impact pads; first means operatively associated with said display means for presenting a visual cue on said replication of said field means at a target intercept position graphically corresponding to one of said plurality of intercept positions different from the current intercept position of the subject; timing means for receiving said signal from said sensor means and determining from the group consisting of (a) the time interval from said visual cue until commencement of movement by the subject for exiting said current interception position, (b) the interval from said commencement of movement until the subject reaches said next interception position; second means for initiating another visual cue when said subject reaches said next intercept position, said second means generating subsequent visual cues in a nonpredictable fashion as to timing and prescribing a course of subject movement between said current intercept position and subsequent intercept positions; and means associated with said timing means for graphically displaying information related to said timing intervals.

4. A method of determining the reaction movement sequence of a player, comprising the steps of: providing a horizontal field engagable by the player and confining movement therewithin; determining the current position of the player on said field; directing the player to a second position on said field; determining a transit time based on the time interval between departure from said current position toward said second position; providing analog sensing means at said second position providing a signal in accordance with changes in movement by said player at said second position; determining from said signal a stabilization time based on the time interval between said arrival at said second position and the player having achieved predetermined stability at said second position; and displaying information based on said time interval subsequent to said arrival at said second position.

5. A functional testing system for determining differences between right directed movement and left directed movement of a subject, comprising: a field consisting of a plurality of target positions defining individually therebetween a set of movement paths substantially balanced between right vectored movement and left vectored movement; sensor means operatively associated with said target positions for determining loading caused by said subject at said target position; display means viewable by said subject at said target positions showing a replication of said field and said target positions; indicating means operatively associated with said display means for representing the current target position of said subject and designating a subsequent target position for said subject; control means operatively associated with said sensor means and said indicating means for establishing a sequential series of target positions comprising said set of movement paths; timing means operatively associated with said sensor means and said indicating means for determining time intervals associated with loading at said target positions during movement therebetween; means operatively associated with said timing means for comparing said time intervals during said sequential series and determining differences in said time intervals between said right directed movement and said left directed movement of said subject.

6. A reaction movement sequence system for directing and assessing leg movement performance of a subject, comprising:
   a. display means;
   b. means for generating a movement cue;
   c. a plurality of intercept positions arrayed in predetermined positions to provide predetermined relationships with respect to the other intercept positions and reachable by lateral, forward and backward movements of the subject;
   d. analog sensor means operatively associated with said intercept positions for providing a signal in accordance with changes in loading on said intercept positions;
   e. timing means for receiving said signal from said sensor means and determining (1) the time interval from said movement cue until commencement of movement by the subject for exiting said current intercept position, (2) the interval from said commencement of movement cue until the subject leaves said current intercept position, and (3) the time interval until said subject reaches predetermined stability on said target intercept position;
   f. means for initiating another movement cue when said subject reaches said intercept position and generating subsequent visual cues prescribing a course of subject movement between said current intercept position and subsequent intercept positions; and
   g. means associated with said timing means and said display means for graphically presenting on said display means information related to said timing intervals.

7. A reaction movement sequence apparatus for directing and assessing leg movement performance of a subject, comprising: a plurality of intercept positions, each intercept position comprising foot impact pads geometrically oriented and arrayed to provide predetermined relationships with respect to the other pads and reachable by lateral, forward and backward movements of the subject; analog sensor means operatively associated with said impact pads providing a signal in accordance with movement on said impact pads; first means for presenting a cue for directing movement to a destination intercept position different from the current intercept position of the subject; timing means for receiving said signal from said sensor means and determining (a) a reaction time based on the time interval from said cue until commencement of movement by the subject for exiting said current interception position, and (b) a ground force time based on the time interval from said commencement of movement until the subject leaves said current intercept position; second means for initiating another cue when said subject reaches said destination intercept position, said second means generating subsequent cues for prescribing a course of subject movement between said current intercept position and subsequent destination intercept positions.

8. A system for determining differences between isolated limbs during horizontal movement of a subject, characterized by a field consisting of a plurality of targets defining non-linear intercept positions requiring horizontal movement to travel therebetween; sensor means operatively associated with said targets for determining changes in loading caused by said subject at said intercept position; control means operatively associated with said sensor means for establishing a sequential series of intercept positions comprising horizontal movements; operatively associated with said sensor means for determining time intervals associated with changes in loading at said intercept positions during movement therebetween; means operatively associated with said timing means for comparing said time intervals during said sequential series and determining differentials between said isolated limbs of said subject.

9. A system for determining stability of a subject horizontally moving from a first position to a second position, comprising: a horizontal platform defining said second position; analog sensor means operatively associated with said platform for generating a signal varying with time and amplitude in response to forces generated by the subject thereon; first means coupled to said sensor means for establishing a predetermined time interval; second means coupled to said sensor means for determining the amplitude of said signal during said time interval and for resetting said time interval if said amplitude exceeds a predetermined amplitude during said time interval; means for indicating stability at said platform when said amplitude does not exceed said predetermined amplitude during said time interval.

10. A method of determining the stability of a limb of a subject horizontally moving from a first position and impacting a second position with said limb, comprising the steps of:
    a. providing a horizontal target at said second position having analog sensor means generating a signal varying in amplitude and time in accordance with forces transmitted by said limb of said subject on said target;
    b. cuing said subject for horizontally moving from said first position and impacting said second position;
    c. continuously evaluating said signal after said impacting as to time and amplitude;
    d. determining from said evaluating when said signal has not exceeded a predetermined amplitude during a predetermined time;
    e. indicating to said subject when said predetermined amplitude has not exceeded said predetermined amplitude during said predetermined time; and
    f. determining the time interval between the time of said impacting and the time when said subject did not exceed said predetermined amplitude during said predetermined time.

11. The method as recited in claim 10 including the further step of cuing said subject after said indicating of step e to move horizontally to another position.

12. A system for directing and assessing leg movement performance of a subject, comprising: display means; a plurality of intercept positions, each intercept position comprising at least one foot impact pad for receiving a foot of the subject, said intercept positions being arrayed on the field in predetermined positions to provide predetermined relationships with respect to the other pads and reachable by lateral, forward and backward movements of the subject; sensor means operatively associated with each of said impact pads for providing a signal in accordance with the presence of the legs of the subject on said impact pads; first means operatively associated with said display means for presenting thereon a representation of said intercept positions; second means operatively associated with said first means for presenting a visual cue on said replication of said field means at a target intercept position corresponding to one of said plurality of intercept positions different from the current intercept position of the subject; timing means for receiving said signal from said sensor means and determining the interval from said visual cue until the subject is present on the impact pads at said target intercept position; third means for initiating another visual cue when said subject reaches said target intercept position, said third means generating subsequent visual cues in a nonpredictable fashion as to timing and prescribing a course of subject movement between said current intercept position and subsequent intercept positions; and means associated with said timing means and said display means for graphically presenting on said display means information related to said time intervals.

13. A method of measuring changes of loading on a limb of a subject during horizontal movement between positions, comprising the steps of: providing on a display means in a non-predictable sequence a spatially related cue directing movement of said limb of said subject from a current position to a subsequent position; measuring changes in loading of said limb during such movement; and providing the subject with information related to such changes in loading.

14. The method as recited in claim 13 wherein said measuring changes in loading is with respect to amplitude and time.

15. The method as recited in claim 13 wherein said measuring determines the time interval between commencement of movement of said limb on said current position until said limb has vacated said current position.

16. The method as recited in claim 13 wherein said measuring determines when said loading of said limb at said subsequent position does not exceed a predetermined amplitude for a predetermined time.

17. The method as recited in claim 13 including the step of locating said positions a predetermined distance apart and measuring the time from commencement of movement by said limb on said current position until initial loading by said limb on said subsequent position.

18. The method as recited in claim 13 including repeating said method using the other limb of said subject.

19. The method as recited in claim 18 including the step of comparing said information between said limbs.

20. A reaction movement sequence system for directing and assessing leg movement performance of a subject, comprising:
 a. a plurality of intercept positions geometrically oriented and arrayed to provide predetermined relationships reachable by movements of the subject;
 b. display means for graphically representing said intercept positions;
 c. first means operatively associated with said display means for presenting on said display means a visual cue of a designated target intercept position graphically corresponding to one of said plurality of intercept positions different from the current intercept position of the subject;
 d. analog sensor means operatively associated with said designated target position providing a signal in accordance with movement thereon;
 e. timing means for receiving said signal from said sensor means and determining the time interval from said subject reaching an intercept position until reaching a predetermined stability thereon;
 f. second means for initiating another visual cue at said designated intercept position and prescribing a course of subject movement therefrom; and
 g. means associated with said timing means for graphically displaying information on said display means related to said time interval.

21. The reaction movement sequence system as recited in claim 20 wherein said analog sensor means are operatively associated with each of said target positions and provide a signal in accordance with movement thereon.

22. The reaction movement sequence system as recited in claim 20 wherein said timing means receives said signal from said sensor means and determines the time interval from said another visual cue until onset of movement by said subject.

23. The reaction movement sequence system as recited in claim 20 wherein said timing means receives said signal and determines the time interval from said another visual cue until said subject departs said designated intercept position.

24. The reaction movement sequence system as recited in claim 20 wherein said current position is provided with sensing means for providing a signal to said said timing means when said subject departs said current position, and said timing means determines the time interval from when said subject departs said designated intercept position until said arrival at said designated intercept position.

25. The method as recited in claim 4 including the step of providing sensing means at said current position generating a signal when said subject departs said current position and said timing means receives such signal and determines a transit time based on the time interval between the departure from said current position until said arrival at said second position.

26. The method as recited in claim 25 including the step of providing sensing means at said current position generating a signal at the onset of movement by said subject at said current position to said second position and said timing means receives such signal and determines a ground force time based on the time interval between said onset and said departure from said current position.

* * * * *